US010470702B2

(12) United States Patent
Whiting et al.

(10) Patent No.: US 10,470,702 B2
(45) Date of Patent: Nov. 12, 2019

(54) ASSIGNING ZONE-BASED RANKINGS AND ACTIONS

(71) Applicant: ZOLL Medical Corporation, Chelmsford, MA (US)

(72) Inventors: Jason T Whiting, Gibsonia, PA (US); Steven J Szymkiewicz, Bethel Park, PA (US)

(73) Assignee: ZOLL Medical Corporation, Chelmsford, MA (US)

(*) Notice: Subject to any disclaimer, the term of this patent is extended or adjusted under 35 U.S.C. 154(b) by 123 days.

(21) Appl. No.: 15/437,954

(22) Filed: Feb. 21, 2017

(65) Prior Publication Data

US 2018/0235537 A1   Aug. 23, 2018

(51) Int. Cl.
| A61B 5/00 | (2006.01) |
| A61B 5/046 | (2006.01) |
| A61B 5/11 | (2006.01) |
| A61N 1/04 | (2006.01) |
| A61N 1/39 | (2006.01) |
| A61N 1/362 | (2006.01) |
| A61N 1/372 | (2006.01) |

(Continued)

(52) U.S. Cl.
CPC ........... *A61B 5/4836* (2013.01); *A61B 5/046* (2013.01); *A61B 5/1118* (2013.01); *A61B 5/6805* (2013.01); *A61B 5/746* (2013.01); *A61N 1/046* (2013.01); *A61N 1/0484* (2013.01); *A61N 1/3621* (2013.01); *A61N 1/3655* (2013.01); *A61N 1/36521* (2013.01); *A61N 1/36564* (2013.01); *A61N 1/36578* (2013.01); *A61N 1/36592* (2013.01); *A61N 1/37247* (2013.01); *A61N 1/37258* (2013.01); *A61N 1/37282* (2013.01); *A61N 1/3987* (2013.01); *A61B 5/0022* (2013.01); *A61B 5/02438* (2013.01); *A61B 5/04011* (2013.01); *A61B 5/0464* (2013.01)

(58) Field of Classification Search
CPC ... A61B 5/4836; A61B 5/0022; A61B 5/0015; A61N 1/3603; A61N 1/36
See application file for complete search history.

(56) References Cited

U.S. PATENT DOCUMENTS 6,301,502 B1   10/2001  Owen et al.
8,271,072 B2   9/2012   Houben et al.
(Continued)

*Primary Examiner* — Alyssa M Alter
(74) *Attorney, Agent, or Firm* — ZOLL Medical Corporation

(57) ABSTRACT

A system for assigning zone rankings to a patient. The system includes a processor, at least one database, and a computer readable medium in communication with the at least one database and comprising one or more instructions that, when executed, can cause the processor to receive at least one physiological signal from a medical monitoring device that is worn by a patient; assign a normal zone ranking to the patient based upon historical patient data stored on the at least one database; determine one or more metrics from the at least one physiological signal of the patient; assign a first zone ranking to the patient based upon the one or more metrics, the first zone ranking selected from a plurality of abnormal zone rankings stored on the at least one database; determine one or more actions to initiate based upon the assigned first zone ranking; and initiate the one or more determined actions.

27 Claims, 13 Drawing Sheets

(51) Int. Cl.
*A61N 1/365* (2006.01)
*A61B 5/024* (2006.01)
*A61B 5/0464* (2006.01)
*A61B 5/04* (2006.01)

(56) References Cited

U.S. PATENT DOCUMENTS

| | | |
|---|---|---|
| 8,774,917 B2 | 7/2014 | Macho et al. |
| 2004/0133119 A1 | 7/2004 | Osorio et al. |
| 2015/0213233 A1 | 7/2015 | Fleming et al. |
| 2015/0250428 A1* | 9/2015 | Zhang .................. G16H 50/30 600/301 |
| 2015/0342540 A1 | 12/2015 | An et al. |

* cited by examiner

|  | Zone 1 | Zone 2 | Zone 3 | Zone 4 |
|---|---|---|---|---|
| Immediate Response | 506 | 510 | 514 | 518 |
| Long-Term Response | 508 | 512 | 516 | 520 |

FIG. 5

| Zone Ranking | Zone 1 | Zone 2 | Zone 3 | Zone 4 | Zone 5 | Zone 6 | Zone 7 |
|---|---|---|---|---|---|---|---|
| Heartrate | 31-89 | 90-119 | 120-169 | 170-200 | Above 200 | 20-30 | Below 20 |
| Severity Level | None | Low | Medium | High | Very High | High | Very High |
| Immediate Response | Continue Monitoring | Continue Monitoring | Provide Instructions | Prepare for Treatment | Provide Treatment | Prepare for Treatment | Provide Treatment |
| Long-Term Response | Continue Monitoring | Additional ECG Recordings | Additional ECG Analysis | Notify Physician | Notify Emergency Personnel | Notify Physician | Notify Emergency Personnel |

ASSIGNING ZONE-BASED RANKINGS AND ACTIONS

BACKGROUND

The present disclosure is directed to medical therapy systems, and more particularly, to medical devices configured to monitor one or more physiological signals for a patient and, based upon the monitored signals, perform one or more actions.

There are a wide variety of electronic and mechanical devices for monitoring and treating patients' medical conditions. In some examples, depending on the underlying medical condition being monitored or treated, medical devices such as cardiac monitors or defibrillators may be surgically implanted or externally connected to the patient. In some cases, physicians may use medical devices alone or in combination with drug therapies to treat conditions such as cardiac arrhythmias.

One of the most deadly cardiac arrhythmias include ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

Example external cardiac monitoring and/or treatment devices include cardiac monitors, the ZOLL LifeVest® wearable cardioverter defibrillator available from ZOLL Medical Corporation, and the AED Plus also available from ZOLL Medical Corporation.

SUMMARY

A system for assigning zone rankings to a patient is described herein. In certain implementations, the system includes a processor, at least one database, and a computer readable medium in communication with the at least one database and comprising one or more instructions. In some examples, the one or more instructions, when executed, can cause the processor to receive at least one physiological signal from a medical monitoring device that is worn by a patient; assign a normal zone ranking to the patient based upon historical patient data stored on the at least one database; determine one or more metrics from the at least one physiological signal of the patient; assign a first zone ranking to the patient based upon the one or more metrics, the first zone ranking selected from a plurality of abnormal zone rankings stored on the at least one database; determine one or more actions to initiate based upon the assigned first zone ranking; and initiate the one or more determined actions.

In certain implementations of the above system, initiating the one or more determined actions comprises instructing the medical monitoring device to perform the one or more determined action. In some examples, the one or more actions comprises at least one of provide a treatment to the patient, activate an alarm indicating a potential treatment, provide instructions to the patient, and perform additional analysis of the at least one physiological signal of the patient.

In certain implementations of the above system, determining one or more metrics comprises determining a heartrate of the patient. In some examples, the plurality of zone rankings comprises at least a set of rapid heartrate action zones and a set of slow heartrate action zones. In some implementations, the set of rapid heartrate action zones comprises at least a first rapid heartrate zone comprising a heartrate of 90-119 beats per minute, a second rapid heartrate zone comprising a heartrate of 120-169 beats per minute, a third rapid heartrate zone comprising a heartrate of 170-200 beats per minute, and a fourth rapid heartrate zone comprising a heartrate over 200 beats per minute. In some examples, the set of slow heartrate action zones comprises at least a first slow heartrate zone comprising a heartrate of 20-30 beats per minute and a second slow heartrate zone comprising a heartrate under 20 beats per minute.

In certain implementations of the above system, the first zone ranking is selected from a plurality of zone rankings, each of the plurality of zone rankings comprising a severity level. In some examples, the severity level for each of the plurality of zone rankings comprises at least one of low risk, medium risk, high risk, and requires immediate attention.

A wearable medical device is also described herein. In certain implementations, the wearable medical device can include at least one sensing electrode configured to detect at least one physiological signal of a patient, and a monitoring device operatively connected to the at least one sensing electrode. In some examples, the monitoring device can be configured to assign a normal zone ranking to the patient; receive the at least one physiological signal of the patient from the at least one sensing electrode; determine one or more metrics from the at least one physiological signal of the patient; assign a first zone ranking to the patient based upon the one or more metrics, the first zone ranking selected from a plurality of abnormal zone rankings stored on at least one database; determine one or more actions to initiate based upon the assigned first zone ranking; and initiate the one or more determined actions.

In certain implementations of the wearable medical device as described above, the one or more actions comprises at least one of provide a treatment to the patient, activate an alarm indicating a potential treatment, provide instructions to the patient, and perform additional analysis of the at least one physiological signal of the patient.

In certain implementations of the wearable medical device as described above, determining one or more metrics comprises determining a heartrate of the patient. In some examples, the monitoring device is further configured to analyze the heartrate to determine if the patient is experiencing one of bradycardia, ventricular tachycardia and ventricular fibrillation. In some examples, the wearable medical device further includes at least one therapy electrode operably connected to the monitoring device and configured to direct a therapeutic shock to the patient. In certain implementations, the at least one therapy electrode is further configured to direct a defibrillation shock to the patient if the patient is experiencing ventricular fibrillation. In some examples, the at least one therapy electrode is further configured to provide a pacing shock to the patient if the patient is experiencing bradycardia.

In certain implementations of the wearable medical device as described above, the first zone ranking is selected from a plurality of zone rankings, each of the plurality of zone rankings comprising a severity level. In some examples, the severity level for each of the plurality of zone rankings comprises at least one of low risk, medium risk, high risk, and requires immediate attention. In certain implementations, initiating one or more determined actions includes at least one of recording the physiological signal of that patient for a zone with a low risk; recording the physiological signal of the patient and additional patient information for a zone with a medium risk; providing a pacing shock to the patient for a zone with a high risk; and providing a defibrillation shock to the patient for a zone that requires immediate attention. In some examples, providing a pacing shock comprises at least one of providing an antibradycardia pacing shock and providing an antitachycardia pacing shock.

In certain implementations of the wearable medical device as described above, the wearable medical device further includes a user display interface operably connected to the monitoring device and configured to provide information related to the one or more determined actions to the patient. In some examples, the user display interface is configured to provide instructions to the patient.

In certain implementations of the wearable medical device as described above, the wearable medical device further includes an accelerometer to measure motion associated with the sensing electrode, wherein the monitoring device is configured to receive data representing the measured motion. In some examples, the monitoring device is further configured to determine a level of exertion associated with the patient based upon the received data representing the measured motion and adjust the plurality of zone rankings based upon the determined level of exertion.

A second system for assigning zone rankings to a patient is also described herein. The second system includes a wearable medical device and a remote computing device. The wearable medical device includes at least one sensing electrode configured to detect at least one physiological signal of a patient, and a monitoring device operatively connected to the at least one sensing electrode. In some examples, the monitoring device is configured to receive the at least one physiological signal of the patient from the at least one sensing electrode and transmit the at least one physiological signal. The remote computing device includes a processor, at least one database, and a computer readable medium in communication with the at least one database and comprising one or more instructions. In some examples, the one or more instructions, when executed, can cause the processor to establish communications with the monitoring device; receive at least one physiological signal from the monitoring device; assign a normal zone ranking to the patient based upon historical patient data stored on the at least one database; determine one or more metrics from the at least one physiological signal of the patient; assign a first zone ranking to the patient based upon the one or more metrics, the first zone ranking selected from a plurality of abnormal zone rankings stored on the at least one database; determine one or more actions to initiate based upon the assigned first zone ranking; and initiate the one or more determined actions.

In certain implementations of the above second system, initiating the one or more determined actions comprises instructing the wearable medical device to perform the one or more determined action. In some examples, the one or more actions comprises at least one of provide a treatment to the patient, activate an alarm indicating a potential treatment, provide instructions to the patient, and perform additional analysis of the at least one physiological signal of the patient.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of any particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 5 depicts a sample table for determining one or more actions to take for an assigned zone ranking, in accordance with an example of the present disclosure.

FIG. 9 depicts a sample table for determining one or more actions to take for an assigned zone ranking organized according to measured heartrate, in accordance with an example of the present disclosure.

DETAILED DESCRIPTION

Figure 1:
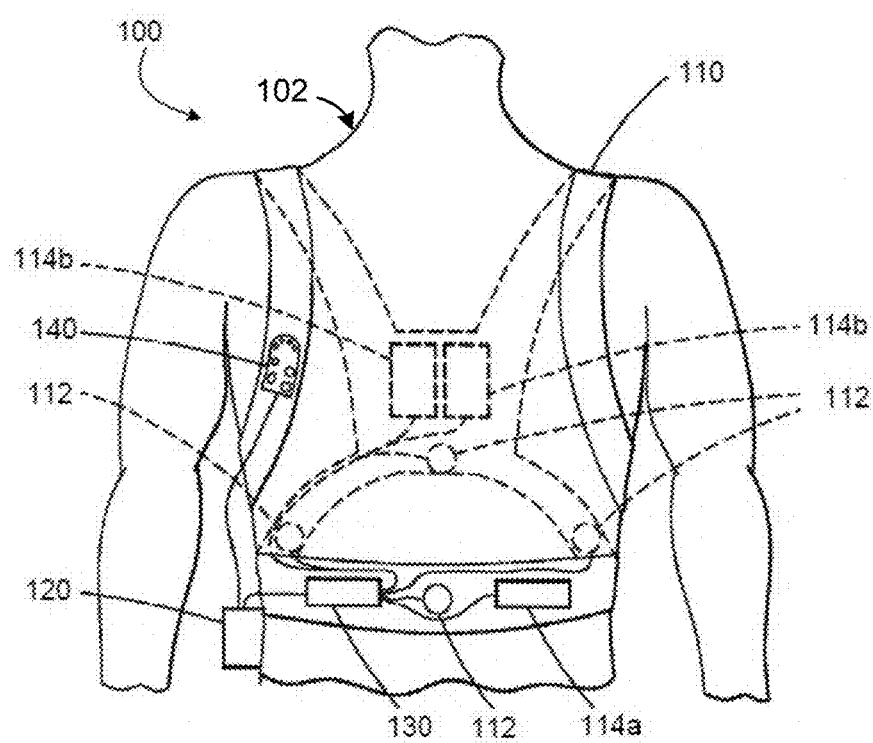
FIG. 1 depicts a wearable medical device, in accordance with an example of the present disclosure.

As used herein, the singular form of "a", "an", and "the" include plural referents unless the context clearly dictates otherwise. Similarly, as used herein, the terms "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention can assume various alternative orientations and, accordingly, such terms are not to be considered as limiting. Also, it is to be understood that the invention may assume various alternative variations and stage sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Accordingly, unless indicated to the contrary, the numerical parameters set forth in the following specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

This disclosure relates to improving the functionality of a medical device, for example, a cardiac monitoring device, by customizing device actions and responses to a cardiac event based upon the patient and/or clinical need. For example, based upon monitoring physiological signals and related events, the medical device can classify an event into one of a set of various zones. In certain implementations, the zones can be defined by heartrate, stability, conduction vector, and other similar parameters or metrics that can be obtained, measured or determined from monitoring one or more physiological signals (e.g., an ECG signal) for a patient. The zones can be programmed with various actions and responses. In certain implementations, the zones can have a specific listing or set of actions and responses to perform when the patient is determined to be in that zone. For example, the zones can have specific ECG recording options, alarm options, sets of instructions to display to a patient or a caregiver, treatment regimens/options, and other similar actions and responses as described below in greater detail. Within each of the different zones, the medical device can be programmed to perform one or more actions according to the specific listing or set of actions and response for that zone. If, for example, a patient transitions from one zone to another, the medical device can be programmed to change actions and responses to reflect the patient's transition from one zone to another.

The disclosure also relates to additional processing of patient information recorded by, for example, a cardiac monitoring device, where the additional processing is performed at a remote location. For example, determining a patient's current zone ranking, effecting a patient transition from one zone to another, actions to be carried out based upon a patient's determined zone rankings, and other similar processing tasks can be performed at a remote location such as a patient management server or system located, for example, at a medical care facility, at the manufacturer of the cardiac monitoring device, or other authorized location.

Currently measured metrics or detected cardiac events for a patient can be compared to stored zone thresholds associated with a corresponding zone ranking to determine a plan of action or response to the currently measured metrics or detected cardiac events. The plan of action or response can vary based on a severity level associated with an associated zone ranking. Accordingly, a determined plan of action or a response for a zone having a lower severity level can differ from a determined plan of action or a response for a zone having a higher level of severity. For example, a patient experiencing a slightly elevated heartrate can have a different plan of action that a patient experiencing ventricular tachycardia ("VT") or ventricular fibrillation ("VF").

Systems and methods are detailed herein and often described with respect to patients who are at risk of a cardiac event; however, disclosed embodiments are not limited only to cardiac events. Systems and methods described herein can be used for detection and zone-based ranking of any measurable metric or detectable medical event based on any monitored physiological parameter of a patient, either alone, or together with one or more cardiac events.

Patients who may be at risk of a cardiac event, for example, cardiac arrest, VT, VF, pulseless electrical activity ("PEA"), asystole, among other cardiac arrhythmias, can be monitored for indications of an oncoming cardiac event so that actions can be taken to reduce the probability of the occurrence of the cardiac event and/or mitigate harm to the patient due to the cardiac event. By utilizing a process of assigning a zone ranking having an associated severity level and one or more actions to initiate, alternative and customized treatment options can be provided for an individual patient rather than having a single set actions to perform for all patients. An event estimation of risk score can be determined for any combination of such cardiac events. The patients to be monitored can include patients that have experienced a cardiac event in the past, patients that are recovering from cardiac or other surgery, and/or patients that have indicated other signs of possible cardiac dysfunction, for example, an otherwise unexplained loss of consciousness, syncope, rapid heartbeat, or chest pain.

An external medical device as described herein can include, but is not limited to, one or more cardiac sensing electrodes, a controller, and a user interface. The cardiac sensing electrode monitors cardiac electrophysiology and can be used to obtain electrocardiogram (ECG) records such as the p, q, r, s, t, and u waves as well as premature ventricular contraction, tachyarrhythmia and changes to heart wave morphology. These ECG records along with related information derived from the heart rhythm data can be used alone or in combination with demographic and medical history to classify a patient for elevated risk of sudden cardiac death which can result from sudden cardiac arrest or asystole. The controller can be adjusted to analyze a combination of cardiac electrophysiology and patient data, including information garnered from ECG recordings of several hours to as little as 45 seconds or less. ECG recordings can be obtained once per patient, multiple times, or continuously during the course of a patient's wearing of the device. For example, continuous recordings can include substantially continuous recordings of the patient's ECG where the recordings are only interrupted, e.g., to allow for restoration of connectivity to a base station or remote server, to change electrodes attached to the patient, replace batteries, or take other such actions. For example, in implementations involving multiple or continuous recordings, a time dependent measure of changes to a zone ranking can be obtained. The user interface can provide a visual display screen with audio and vibrational components, as well as cellular and wireless internet connectivity, any or all of which can be used as a means to provide a summary of information to the patient, first responder, or medical professional.

In an implementation, systems, methods, and devices as described herein can be used for classifying patients by a zone-based ranking and initiating a plan of action based upon a severity level associated with an assigned zone. For example, the principles described herein can be implemented in cardiac monitoring and/or therapeutic devices. For instance, the principles as described herein relate generally to a cardiac monitoring device used, for example, in mobile cardiac telemetry (MCT), continuous event monitoring (CEM) applications, and an implantable cardioverter defibrillator (ICD).

In some implementations, at least one embodiment relates generally to an ambulatory therapeutic device, and more specifically to a wearable therapeutic device configured to monitor a patient's cardiac electrophysiology such as a wearable cardioverter defibrillator. An embodiment incorporates the patient's ECG along with demographic information and medical history (such as gender, age, left ventricular ejection fraction, co-morbidities and cardiac indications leading to prescription of the wearable therapeutic device).

Parameters or metrics of a patient that can be monitored include various parameters of the patient's ECG signal. ECG signal parameters can include, for example, changes to the T-wave such as T-wave alternans or T-wave lability (e.g., morphological changes in the T-wave not limited to alternating beats, but occurring every, e.g., third, fourth, fifth, etc. beat), PR interval, QT interval, QRS complex, heartrate variability (HRV), and/or other parameters of the ECG signal of a patient.

A non-exhaustive list of other measurable parameters or metrics of a patient that can be monitored and evaluated for assigning a zone ranking to a patient can include a low and decreasing hear rate, (e.g., bradycardia, commonly referred to as "Bradying down"), increased heartrate (e.g., tachycardia), blood pressure, change in conduction vector, change in heartrate stability, tidal $CO_2$, (i.e., the concentration or partial pressure of carbon dioxide in the respiratory gases of the patient), $SpO_2$, (i.e., a measure of blood oxygen saturation), $SMO_2$, (i.e., a measure of muscle oxygen saturation), cerebral blood flow, electroencephalography (EEG) signals, electromechanical activation time (EMAT) (as described in further detail below), heart sounds (e.g., S3 and S4 sounds), brain oxygen level, (i.e., cerebral oximetry), tissue pH, ultrasound images of the patient's heart, and a reaction of the patient's heartrate to tilting of the patient.

Parameters and metrics of a patient that can be monitored for an indication of an oncoming cardiac event can be monitored invasively or non-invasively, and many parameters of the patient can be monitored using optical techniques. For example, sublingual $CO_2$, brain oxygen level and tissue pH can be measured optically.

Measurable parameters or metrics based on heart sounds can include acoustic cardiographic metrics derived from acquisition and quantitative measurements of combined ECG and cardiac acoustical data. Such metrics can include those that identify and quantify normal and abnormal heart sounds, e.g., related to the left ventricle, and indicate the timing of those heart sounds in every cardiac cycle versus the onset of the P wave and QRS complexes in a substantially simultaneously recorded ECG. For example, such metrics can indicate the presence and strength of heart sounds (such as the S3 and S4) and the duration of systolic time intervals.

In some examples, such acoustic and/or combined acoustic and ECG metrics can include electromechanical activation time (EMAT) metrics. For example, EMAT metrics as used herein describe an interval from some fiducial timepoint in the electrocardiograph (ECG) to some fiducial timepoint in a subsequent mechanical activity of the heart. One example of a fiducial timepoint in the ECG is an onset of the P-wave and QRS complexes such as the P-wave, Q-wave, R-wave, or S-wave.

An example of a mechanical activity of the heart can be a valve closure, e.g., the closure of the aortic valve. In some examples, the mechanical activity can be left ventricular wall motion, and the fiducial timepoint can be the timepoint of maximal left ventricular wall motion, or the fiducial timepoint might be the start of relaxation. The fiducial timepoint in a subsequent mechanical activity of the heart can be measured by heart sounds, as exemplified by AUDICOR® Technology from Inovise Medical of Beaverton, Oreg., or using ultrasound measurements of ventricular or valvular motion. In some implementations, an example of the fiducial timepoint in a subsequent mechanical activity of the heart can be the timepoint of peak intensity of the S1 heart sound.

The teachings of the present disclosure can be generally applied to external medical monitoring and/or treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, mobile telemetry devices, and other similar wearable medical devices.

The wearable medical device is capable of continuous use by the patient. The continuous use may be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device can be configured to be worn by a patient for as many as 24 hours a day. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, heart sounds, etc.) and/or non-cardiac information (e.g., blood oxygen, the patient's temperature, glucose levels, tissue fluid levels, and/or lung sounds). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, lung sounds (e.g., using microphones and/or accelerometers), breath sounds, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

In some implementations, the medical device may be a patient monitoring device with no treatment or therapy functions. For example, such a patient monitoring device can include a cardiac monitoring device or a cardiac monitor that is configured to monitor one or more cardiac physiological parameters of a patient, e.g., for remotely monitoring and/or diagnosing a condition of the patient. For example, such cardiac physiological parameters may include a patient's electrocardiogram (ECG) information, heart sounds (e.g., using accelerometers or microphones), and other related cardiac information. A cardiac monitoring device is a portable device that the patient can carry around as he or she goes about their daily routine. The cardiac monitor may be configured to detect the patient's ECG through a plurality of cardiac sensing electrodes. For example, a cardiac monitor may be attached to a patient via at least three adhesive cardiac sensing electrodes disposed about the patient's torso. Such cardiac monitors are used in mobile cardiac telemetry (MCT) and/or continuous cardiac event monitoring applications, e.g., in patient populations reporting irregular cardiac symptoms and/or conditions. Example cardiac conditions can include atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. For example, such patients may be prescribed a cardiac monitor for an extended period of time, e.g., 10 to 30 days, 10 to 45 days, or 10 to 60 days. The prescribed period of time may be longer or shorter than those periods described here based on individual patients' needs and/or prescriber preferences. In some mobile cardiac telemetry applications, a portable cardiac monitor can be configured to substantially continuously monitor the patient for a cardiac event (e.g., a cardiac anomaly), and when such an event is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom). The cardiac monitor can be configured to monitor physiologic parameters of the patient other than cardiac related parameters. For example, the cardiac monitor can be configured to monitor, for example, heart sounds (e.g., using accelerometers or microphones), lung sounds, breath sounds, sleep related parameters (e.g., snoring, sleep apnea), tissue fluids, among others.

Example Wearable Medical Devices

FIG. 1 illustrates an example medical device 100 that is external, ambulatory, and wearable by a patient 102, and configured to implement one or more configurations described herein. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., ECG electrodes), one or more therapy electrodes 114, a medical device controller 120, a connection pod 130, a patient interface pod 140, a belt 150, or any combination of these. In some examples, at least some of the components of the medical device 100 can be configured to be affixed to the garment 110 (or in some examples, permanently integrated into the garment 110), which can be worn about the patient's torso.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and therapy electrodes 114 can be included on a single integrated patch and adhesively applied to the patient's body.

The sensing electrodes 112 can be configured to detect one or more cardiac signals. Examples of such signals include ECG signals, heart sounds, and/or other sensed cardiac physiological signals from the patient. The sensing electrodes 112 can also be configured to detect other types of patient physiological parameters, such as tissue fluid levels, lung sounds, respiration sounds, patient movement, etc. Example sensing electrodes 112 include a metal electrode with an oxide coating such as tantalum pentoxide electrodes, as described in, for example, U.S. Pat. No. 6,253,099 entitled "Cardiac Monitoring Electrode Apparatus and Method," the content of which is incorporate herein by reference.

In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the medical device controller 120. One or more therapy electrodes 114 can be configured to deliver one or more therapeutic defibrillating shocks to the body of the patient 102 when the medical device 100 determines that such treatment is warranted based on the signals detected by the sensing electrodes 112 and processed by the medical device controller 120. Example therapy electrodes 114 can include conductive metal electrodes such as stainless steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

WMD/WCD Controller Description

Figure 2:
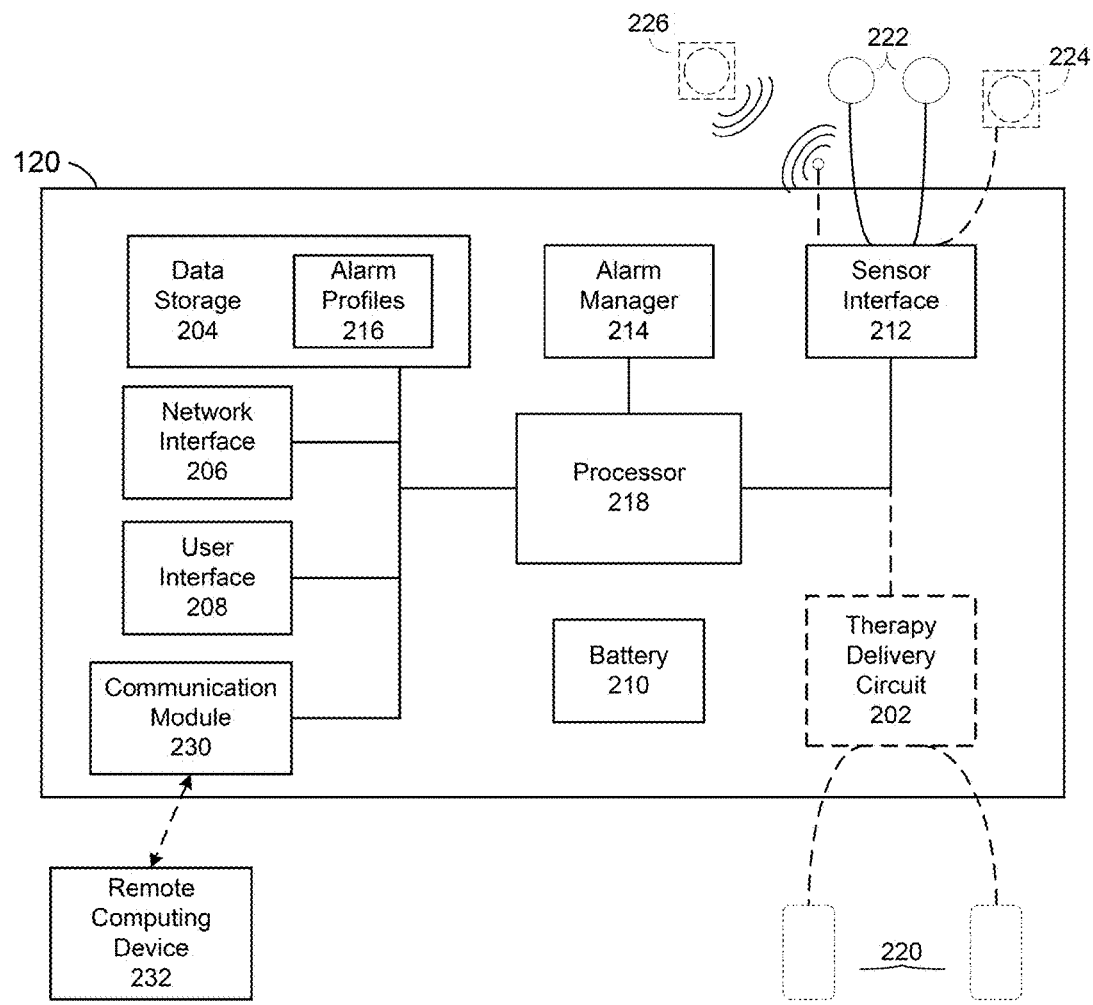
FIG. 2 depicts a schematic view of a sample controller for a wearable medical device such as that shown in FIG. 1, in accordance with an example of the present disclosure.

FIG. 2 illustrates a sample component-level view of the medical device controller 120. As shown in FIG. 2, the medical device controller 120 can include a therapy delivery circuit 202, a data storage 204 (that includes, for example, alarm profile information 216), a network interface 206, a user interface 208, at least one battery 210, a sensor interface 212, an alarm manager 214, and least one processor 218. A patient monitoring medical device can include a medical device controller 120 that includes like components as those described above, but does not include the therapy delivery circuit 202 (shown in dotted lines).

The therapy delivery circuit 202 can be coupled to one or more electrodes 220 configured to provide therapy to the patient (e.g., therapy electrodes 114a-b as described above in connection with FIG. 1). For example, the therapy delivery circuit 202 can include, or be operably connected to, circuitry components that are configured to generate and provide the therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuit and under control of one or more processors (e.g., processor 218) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). These capacitors can be switched into a series connection during discharge for a defibrillation pulse. For example, four capacitors of approximately 650 of can be used. The capacitors can have between 350 to 500 volt surge rating and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuit 202 can be configured to perform the switching and pulse delivery operations, e.g., under control of the processor 218. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 120. In certain implementations, the data storage can include executable instructions that, when executed, are configured to cause the processor 218 to perform one or more functions.

In some examples, the network interface 206 can facilitate the communication of information between the medical device controller 120 and one or more other devices or entities over a communications network. For example, where the medical device controller 120 is included in an ambulatory medical device (such as medical device 100), the network interface 206 can be configured to communicate with a remote computing device such as a remote server or other similar computing device.

In certain implementations, the user interface 208 can include one or more physical interface devices such as input devices, output devices, and combination input/output devices and a software stack configured to drive operation of the devices. These user interface elements may render visual, audio, and/or tactile content, including content relating to location-specific processing. Thus the user interface 208 may receive input or provide output, thereby enabling a user to interact with the medical device controller 120.

The medical device controller 120 can also include at least one battery 210 configured to provide power to one or more components integrated in the medical device controller 120. The battery 210 can include a rechargeable multi-cell battery pack. In one example implementation, the battery 210 can include three or more 2200 mAh lithium ion cells that provides electrical power to the other device components within the medical device controller 120. For example, the battery 210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 212 can be coupled to one or more sensors configured to monitor one or more physiological parameters of the patient. As shown, the sensors may be coupled to the medical device controller 120 via a wired or wireless connection. The sensors can include one or more electrocardiogram (ECG) electrodes 222 (e.g., similar to sensing electrodes 112 as described above in connection with FIG. 1), heart sounds sensors 224, and tissue fluid monitors 226 (e.g., based on ultra-wide band radiofrequency devices).

The ECG electrodes 222 can monitor a patient's ECG information. For example, the ECG electrodes 222 can be conductive and/or capacitive electrodes configured to measure changes in a patient's electrophysiology to measure the patient's ECG information. The ECG electrodes 222 can transmit information descriptive of the ECG signals to the sensor interface 212 for subsequent analysis.

The heart sounds sensors 224 can detect a patient's heart sound information. For example, the heart sounds sensors 224 can be configured to detect heart sound values including any one or all of S1, S2, S3, and S4. From these heart sound values, certain heart sound metrics may be calculated, including any one or more of electromechanical activation time (EMAT), percentage of EMAT (% EMAT), systolic dysfunction index (SDI), and left ventricular systolic time (LVST). The heart sounds sensors 224 can include an acoustic sensor configured to detect sounds from a subject's cardiac system and provide an output signal responsive to the detected heart sounds. The heart sounds sensors 224 can also include a multi-channel accelerometer, for example, a three channel accelerometer configured to sense movement in each of three orthogonal axes such that patient movement/body position can be detected and correlated to detected heart sounds information. The heart sounds sensors 224 can transmit information descriptive of the heart sounds information to the sensor interface 212 for subsequent analysis.

The tissue fluid monitors 226 can use radio frequency (RF) based techniques to assess fluid levels and accumulation in a patient's body tissue. For example, the tissue fluid monitors 226 can be configured to measure fluid content in the lungs, typically for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 212 for subsequent analysis.

The sensor interface 212 can be coupled to any one or combination of sensing electrodes/other sensors to receive other patient data indicative of patient parameters. Once data from the sensors has been received by the sensor interface 212, the data can be directed by the processor 218 to an appropriate component within the medical device controller 120. For example, if heart data is collected by heart sounds sensor 224 and transmitted to the sensor interface 212, the sensor interface 212 can transmit the data to the processor 218 which, in turn, relays the data to a cardiac event detector. The cardiac event data can also be stored on the data storage 204.

In certain implementations, the alarm manager 214 can be configured to manage alarm profiles, such as the alarm profile information 216, and notify one or more intended recipients of events specified within the alarm profiles as being of interest to the intended recipients. These intended recipients can include external entities such as users (patients, physicians, and monitoring personnel) as well as computer systems (monitoring systems or emergency response systems). For example, as noted above, based upon a patient's measured heart-rate, a wearable medical device can determine that the patient currently falls into a specific heart-rate zone. Based upon this zone, a targeted alarm can be provided to the intended recipient. These intended recipients can include external entities such as users (patients, physicians, and monitoring personnel) as well as computer systems (monitoring systems or emergency response systems).

The alarm manager 214 can be implemented using hardware or a combination of hardware and software. For instance, in some examples, the alarm manager 214 can be implemented as a software component that is stored within the data storage 204 and executed by the processor 218. In this example, the instructions included in the alarm manager 214 can cause the processor 218 to configure alarm profiles and notify intended recipients using the alarm profiles. In other examples, alarm manager 214 can be an application-specific integrated circuit (ASIC) that is coupled to the processor 218 and configured to manage alarm profiles and notify intended recipients using alarms specified within the alarm profiles. Thus, examples of alarm manager 214 are not limited to a particular hardware or software implementation.

The alarm profile information 216 can include data used by the alarm manager 214 to notify intended recipients of events of interest. More particularly, according to the illustrated example, the alarm profile information 216 can include information that identifies events of interest, characteristics of one or more alarms used to report the identified events and one or more adaptation paths for each of the one or more alarms. Events of interest can include any event detectable by the wearable medical device controller 120. However, in broad terms, events of interest can be categorized as concerning the patient wearing the wearable medical device, such as an indication of a physiological abnormality in the patient, or concerning the wearable medical device itself, such as a component in need of service (for example, a low battery).

Common alarm characteristics can include an alarm identifier, an intended recipient of the alarm, one or more potential responses, a conduit through which the alarm is provided, content for the alarm, an intensity with which the content is communicated, an issuance rate at which the content is communicated and a target response time. The conduits through which alarms can be issued include, among others, the user interface 208, the network interface 206 and the therapy delivery interface 202.

As illustrated in FIG. 2, the alarm manager 214 and the alarm profile information 216 can be separate components. However, in other examples, the alarm manager 214 and the alarm profile information 216 can be combined into a single component or re-organized so that a portion of the data included in the alarm manager 214, such as executable code that causes the processor 218 to adapt a triggered alarm to a particular patient's heart-rate zone, resides in the alarm profile information 216, or vice versa. Such variations in these and the other components illustrated in FIG. 2 are intended to be within the scope of the examples disclosed herein.

The alarm profile information 216 can be stored in any logical construction capable of storing information on a computer readable medium including, among other structures, flat files, indexed files, hierarchical databases, relational databases or object oriented databases. In addition, various examples can organize the alarm profile information 216 into particularized and, in some cases, unique structures to perform the functions disclosed herein. In these examples, the data structures can be sized and arranged to store values for particular types of data.

In some implementations, the processor 218 includes one or more processors (or one or more processor cores) that each are configured to perform a series of instructions that result in manipulated data and/or control the operation of the other components of the medical device controller 120. In some implementations, when executing a specific process (e.g., cardiac monitoring), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to specific input stimulus in a specific way and generates a corresponding output based on that input stimulus. In some example cases, the processor 218 can proceed through a sequence of logical transitions in which various internal register states and/or other bit cell states internal or external to the processor 218 may be set to logic high or logic low. As referred to herein, the processor 218 can be configured to execute a function where software is stored in a data store coupled to the processor 218, the software being configured to cause the processor 218 to proceed through a sequence of various logic decisions that result in the function being executed. The various components that are described herein as being executable by the processor 218 can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor. The processor can execute an embedded operating system, and include services provided by the operating system that can be used for file system manipulation, display & audio generation, basic networking, firewalling, data encryption and communications.

In some examples, the medical device controller 120 can include communication circuitry, such as communications module 230, for communicating with one or more remote computing devices 232 (e.g., one or more remote computer systems or a remote handheld device such as a smartphone, a personal digital assistant, or a tablet device) over a communications network.

In some examples, the medical device controller 120 can periodically (e.g., on a preset schedule) establish a wireless communication (e.g., cellular communication, WiFi or Bluetooth) and send data, such as patient physiological information, to the remote computing device 232 over the network. For example, such physiological information can include, without limitation, patient symptom data (e.g., patient-reported symptoms and/or automatically detected patient information), related cardiac data including premature ventricular contraction (PVC) count, heart rate information, heart sounds data, ECG data (e.g., continuous ECG data), lung fluid measurements/data, patient thoracic impedance measurements/data, pectoral impedance measurements/data, blood pressure, temperature, blood glucose levels, and blood oxygen levels. In certain implementations, the medical device controller 120 can be configured to establish a continuous connection with a remote computing device via a wide area network such as a cellular data network. In such a scenario, the medical device controller 120 can be configured to establish the communications upon being powered on, reset, or in response to user input to establish communications with a remote device.

In some examples, the medical device controller 120 can be configured to aperiodically establish communication with the remote computing device 232 for the purpose of sending patient data. For example, the physiological data can be processed in accordance to a predetermined standard for transmission and can be transmitted in a secure HIPAA-compliant manner. In some implementations, the cardiac monitoring device 120 can be configured to send information to the remote computing device 232 when a transmission is initiated by the patient. For example, the patient can indicate that he or she is experiencing a symptom.

Determining Zone-Based Actions

As noted above, for various parameters and metrics as measured, monitored, or otherwise determined from a patient's ECG signal, a zone can be assigned to that parameter and/or metric, the zone being representative of various factors such as, for example, the severity or likelihood of a cardiac event occurrence. For example, a patient's heartrate can be determined from their ECG signal. Based upon their current heartrate, the patient can be assigned to a heartrate zone and, if appropriate, an action can be initiated based upon the assigned zone.

Figure 3:
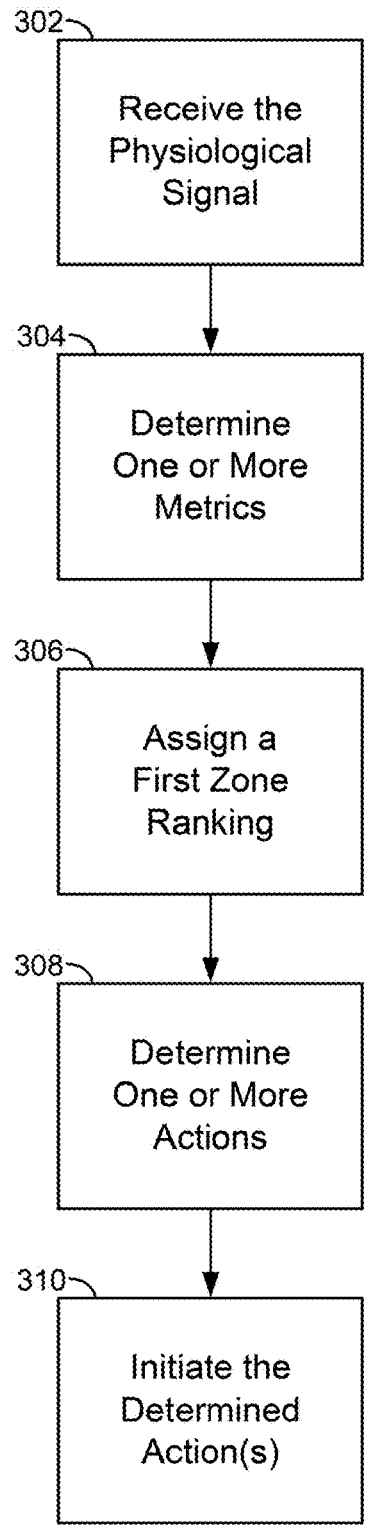
FIG. 3 depicts a sample process for assigning a zone ranking to a patient, in accordance with an example of the present disclosure.

FIG. 3 illustrates a sample flowchart showing a process for determining a zone-based action for a patient wearing an ambulatory medical device, such as a cardiac monitoring device or a wearable cardioverter defibrillator. A controller, e.g., wearable medical device controller 120 as described above, can receive 302 a physiological signal from one or more components of the medical device such as one or more sensing electrodes and/or conditioning circuitry configured to condition a signal measured by the one or more sensing electrodes. In certain implementations, the controller can assign a patient a normal zone ranking based upon historic or baseline information. For example, the normal zone ranking can include normal levels or values for one or more metrics or parameters to be analyzed from the physiological signal based upon the patient's historic or baseline information.

The controller can analyze the physiological signal to determine 304 one or more parameters or metrics indicated or quantified within the physiological signal. The one or more metrics can be indicative of the current cardiac state of the patient. In certain implementations, the one or more metrics can include the heartrate or change in heartrate of the patient, blood pressure of the patient, heartrate stability, changes in conduction vector of the heart, heart sounds information, and other similar metrics such as those listed above.

Based upon the one or more metrics, the controller can assign 306 a first zone ranking for the patient. A zone ranking can include a zone identifier (e.g., zone 1, zone 2, zone 3) as well as an associated severity level. For example, zone 1 can be associated with a low severity level, zone 2 can be associated with a medium severity level, and zone 3 and higher can be associated with a high severity level. Similarly, each severity level can have an associated set of one or more actions to initiate. Zone rankings, severity levels and associated actions are described in greater detail below in the specific examples.

Depending upon the implementation of the zone-based ranking system, a single zone ranking can be associated with the patient. For example, the current determined levels for the one or more metrics can be averaged together to assign a single zone ranking. In other implementations, the patient can be assigned a zone ranking for each metric measured, and the assigned zone ranking with the highest associated severity level can be prioritized such that any actions associated with that zone ranking are implemented first.

Referring again to FIG. 3, the controller can determine 308 one or more actions based upon the assigned first zone ranking. For example, the one or more actions can include provide a treatment to the patient, activate an alarm indicating a potential treatment, assign a predetermined alarm sequence (e.g., assigning an alarm profile) to the patient, provide instructions to the patient, record a portion of the patient's ECG signal, contact emergency services or the patient's physician, perform additional analysis of the patient's ECG signal, and other various actions. For example, a predetermined alarm profile can be based on a predetermined order or sequence of various alarm types such as a vibration alarm, one or more audible alarms (e.g., a gong alarm, a siren alarm, a buzzing alarm, or other audible alarms), voice alarms, and/or visual alarms. The assigned alarm profile may also omit one or more of the foregoing alarm types, and/or change a duration of one or more of the foregoing alarms. Once determined, the controller can initiate 310 the one or more determined actions.

As noted above, an assigned zone ranking can also have an associated severity level. Additionally, when assigning a zone ranking to a patient, the controller can also determine a confidence level. The confidence level can be used to determine whether an action is appropriate for a specific assigned zone ranking at a particular time. For example, when a zone ranking is assigned that has a high severity level with a treatment action associated (e.g., provide a defibrillation pulse), the controller can perform an additional analysis to confirm that the assigned zone ranking is accurate (e.g., based on the determined confidence level) and that the recommended action is appropriate.

Figure 4:
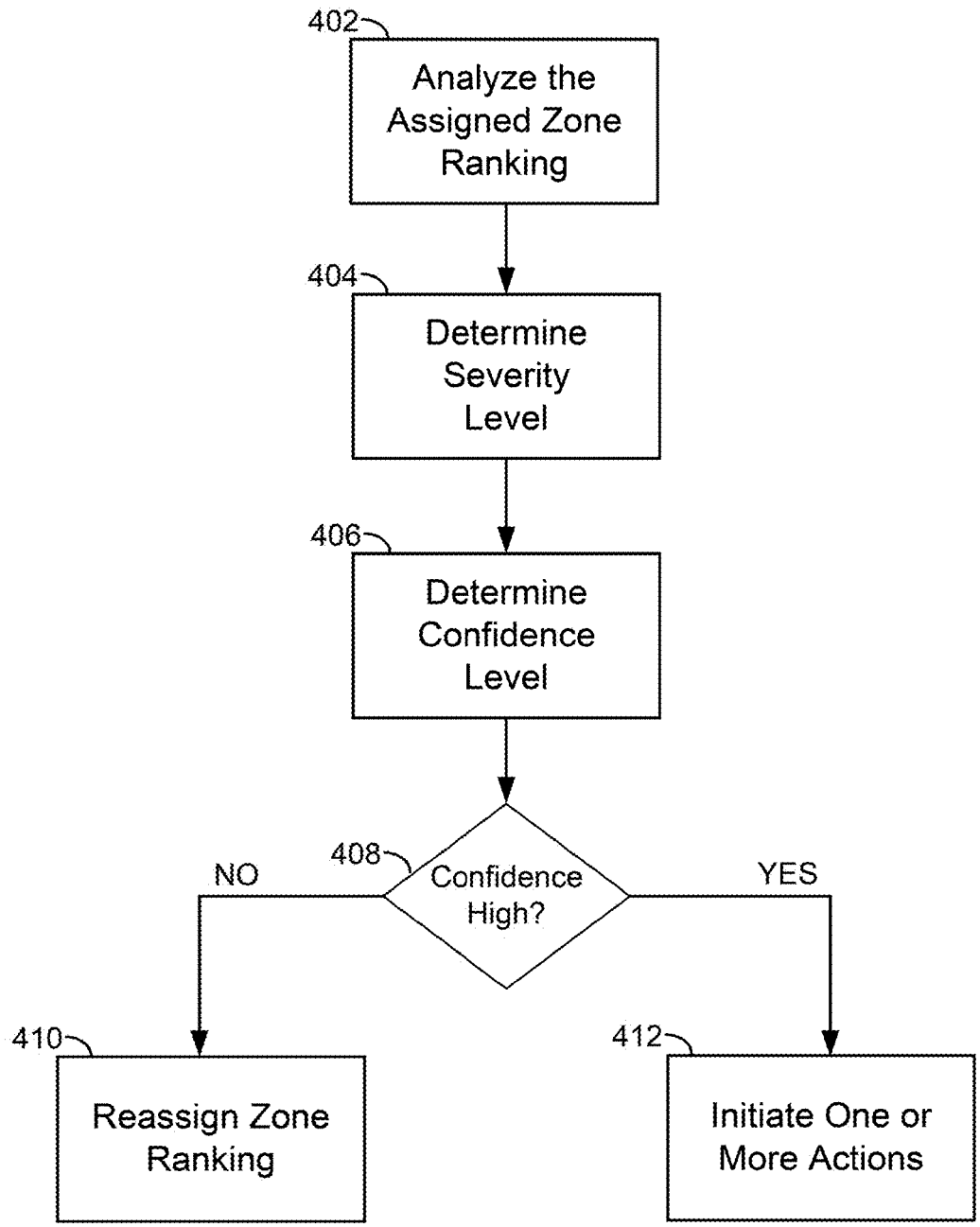
FIG. 4 depicts a sample process for determining a confidence level for an assigned zone ranking, in accordance with an example of the present disclosure.

FIG. 4 illustrates a sample process for determining a confidence level of an assigned zone ranking. Such a process can be implemented in the flowchart of FIG. 3, for example, between the controller determining 308 one or more actions and the controller initiating 310 the one or more determined actions. As shown in FIG. 4, the controller can perform additional analysis 402 of the assigned zone ranking. For example, the controller can perform a redundant analysis of the patients ECG signal to determine the one or more metrics being monitored and confirm that the metrics are still within the currently assigned zone ranking. The controller can then further determine 404 the associated severity level of the assigned zone ranking. As noted above, the severity level can provide an indication of what type of course of action is to be initiated. When implemented, the severity level can be a numerical value such as a value between 0.0 and 1.0. As the severity value increases, so to can the severity of the course of action associated with that zone ranking. For example, a severity level between 0.0 and 0.24 can be low risk and can be associated with lower risk actions such as provide the patient with instructions to alter their physical activity, perform additional signal analysis, perform additional ECG recording, and other similar low risk actions. A severity level between 0.25 and 0.49 can be considered moderate or medium risk and can be associated with medium risk actions such as provide an audible alarm and provide a patient with instructions to take a particular medication. A severity level between 0.50 and 0.74 can be considered high risk and can be associated with higher risk actions such as prepare a device for treatment (e.g., prepare to provide a therapeutic shock) and contacting emergency services. A severity level between 0.75 and 1.00 can be considered very high risk and requires immediate attention. In such a very high risk zone ranking, the medical device can immediately provide treatment to the patient.

Referring again to FIG. 4, for a determined severity level, the controller can also determine 406 a confidence level. Like the severity level, the confidence level can be a numerical value between 0.0 and 1.0. A threshold can be set that indicates whether the confidence level is considered high or low. To determine 406 the confidence level, the controller can perform some additional analysis of the ECG signal as well as process additional information such as historical information and trends information. For example, the controller can determine whether the patient has been assigned a particular zone ranking multiple times in the past when having similar monitored metrics. Additionally, the controller can perform a redundant analysis of the patient's ECG signal to confirm that the monitored metrics have not changed since the previous determination and assignment of a zone ranking. Based upon the determined confidence level, the controller can determine 408 whether the confidence level is high, e.g., above a particular threshold. If the controller determines 408 that the confidence level is not high, the controller can perform some additional analysis such as reassigning 410 a new zone ranking. If the controller does determine 408 that the confidence level is high, the controller can proceed to initiate 412 the one or more actions associated with the assigned zone ranking.

In certain implementations, the controller can initiate one or more actions based on a combination of the severity (risk) measure and a confidence measure for a cardiac parameter or metric. For example, the controller can perform or recommend one or more actions when each of the severity level and the confidence level satisfy respective severity and confidence thresholds for an associated time period. If one of the severity level or the confidence level does not satisfy its respective threshold, an action may not be initiated or a different action can be initiated.

The thresholds can differ based on the type of action to be recommended and the associated time period. For example, the severity threshold and confidence threshold required to perform the action of informing the wearer that the medical device is performing advanced diagnostics (e.g., additional signal analysis or recording) can be lower than the severity threshold and confidence threshold required to perform an action of warning that a shock administration may be imminent or preparing the device for treatment.

It should be noted that the values described above regarding severity and confidence levels are provided by way of example only and, based upon the implementation of the zone-based ranking system as described herein, can be altered accordingly. Additionally, it should be noted that determining a confidence score can be implemented as an optional feature. For example, determining a confidence score can be limited to occasions where the severity level is determined to be very high.

In order to quickly determine what actions are to be implemented for a particular zone, the controller can access a local lookup table that correlates specific actions with individual assigned zones. For example, as shown in FIG. 5, a table 500 can include various columns 502, each column associated with a specific zone ranking (labeled in table 500 as Zone 1, Zone 2, Zone 3 and Zone 4). Similarly, table 500 can include a set of rows 504, each row including one or more actions for a specific time period. For example, a first row can list immediate response actions and a second row can list long-term response actions for each assigned zone in columns 502. Based upon the design and type of medical device, immediate response actions can include actions that are to be initiated and/or carried out in the next 30 seconds. Similarly, long-term response actions can include actions that are to be initiated and/or carried out in a longer time period such as 1 to 24 hours. However, it should be noted that these time periods are provided by way of example only.

As shown in table 500, each specific assigned zone can have one or more actions for each response time period. For example, Zone 1 has associated action 506 as an immediate response and action 508 as a long-term response. Similarly, Zone 2 has action 510 as an immediate response and action 512 as a long-term response, Zone 3 has action 514 as an immediate response and action 516 as a long-term response, and Zone 4 has action 518 as an immediate response and action 520 as a long-term response.

Remote Server Processing

Figure 6:
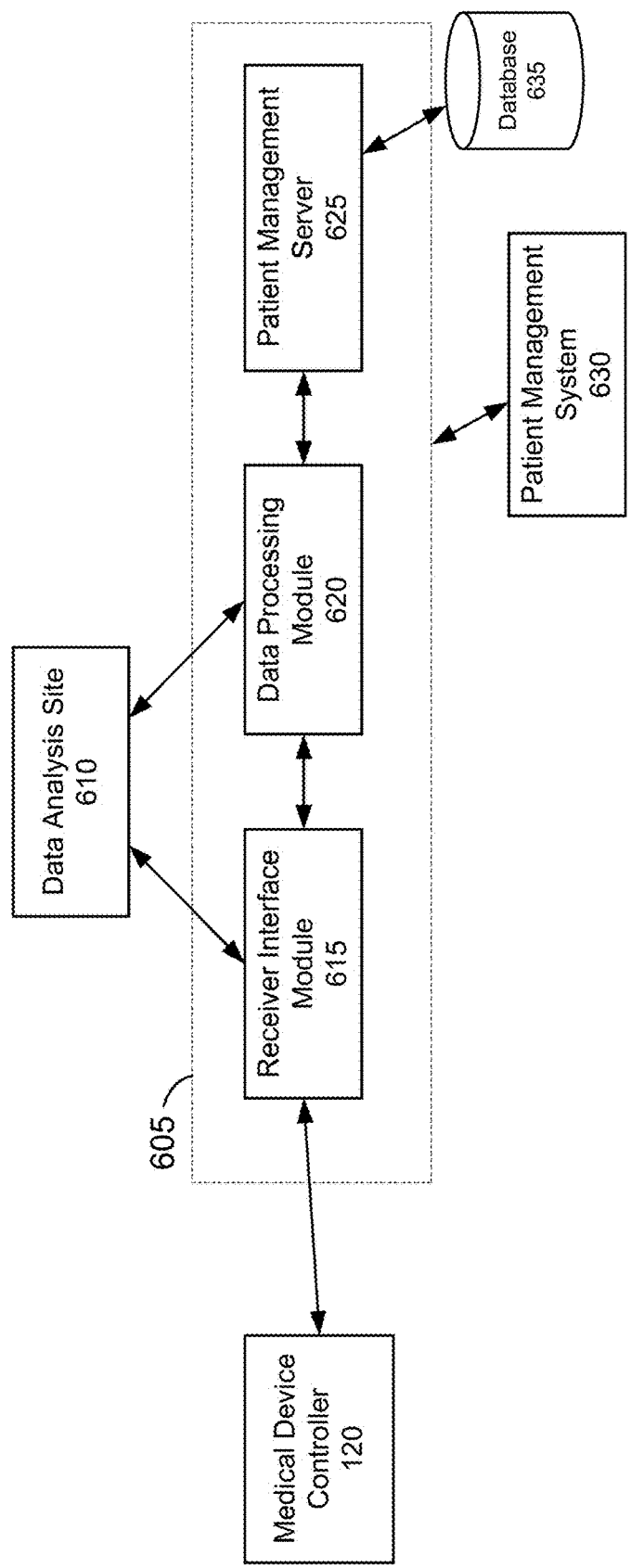
FIG. 6 depicts a schematic drawing of a sample communications network, in accordance with an example of the present disclosure.

The processes and techniques as described above can be optionally implemented at the medical device controller itself or, in certain implementation, at a remote computing device such as a remote server configured to manage patient data and information. FIG. 6 illustrates a sample network topology illustrating an operable connection between a patient's medical device (e.g., medical device controller 120 as shown in FIG. 6) with a remote network 605 including one or more remotely located computing devices.

As shown in FIG. 6, the communications network 605 can be configured to receive the physiological information from the medical device controller 120 to one or more remote locations for analysis and/or review. For example, the communications network 605 can include a reviewer interface module 615, a data processing module 620, and a patient management server 625. It should be noted that the reviewer interface module 615, the data processing module 620, and patient management server 625 can be configured to interface in any manner with the medical devices and/or a data analysis site 610. For example, data received from the medical device controller 120 can first be processed by the data processing module 620 (e.g., as described below, certain analysis can be carried out on the incoming physiological data) and then passed along to the reviewer interface module 615 for further analysis and interpretation in accordance with the disclosure herein. Conversely, data can be reviewed by a reviewer via the reviewer interface module 615 before being processed in the data processing module 620, e.g., reviewer-edited ECG strips from the reviewer interface module 615 can be automatically annotated with pertinent information (e.g., patient information and/or interpretation tools) and sent to the patient management server 625.

In some implementations, the data processing module 620 can be configured to operate independently of the reviewer interface module 615. For example, the data processing module 620 can analyze received data and send any analysis, data, and/or reports to the patient management server 625.

The communications network 605 can include a wired network, a long range wireless network (WiFi), a short-range wireless network (BLUETOOTH®), a cellular network, and/or combinations thereof for transmitting data from the medical device controller 120, between the modules 615, 620, 625, and to the patient management system 630. As described above, the medical device controller 120 can send information over the communications network 605 either substantially continuously or on a preset schedule, based on a request by the patient, automatically based on identification of an event on the device, and/or based on a request from a remote party such as a treating physician.

With continued reference to FIG. 6, the reviewer interface module 615 can be configured to receive information from the medical device controller 120 and, in some examples, to transmit the received physiological information to a data analysis site 610 for review by a technician or reviewer. At the data analysis site 610 (e.g., a mobile telemetry center or system) the patient physiological information collected by the medical device controller 120 is manually reviewed by the technician or reviewer and analyzed for the purpose of identifying and/or confirming any of a number of patient conditions and/or events. For example, events that can be reviewed by the reviewer can include one or more of the following: atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. In certain implementations, the data analysis site 610 can be implemented as an end user terminal operably attached to a remote server or directly connected to, for example, the reviewer interface module 615 and the data processing module 620. For example, the data analysis site 610 can be located at a manufacturer of medical devices, or at a data analysis vendor or other similar vendor contracted by or otherwise associated with the device manufacturer.

In some examples, a reviewer can access the reviewer interface module 615 through an end user terminal that can include, but is not limited to, any one of a: workstation, desktop computer, tablet, smartphone, and/or personal digital assistant. Based upon the desired functionality of the end user terminal, the terminal can include, for example, multiple displays such that the reviewer can run multiple applications for viewing reports related to distinct medical devices. Similarly, the end user terminal can be configured to run multiple instances of the same application, each instance accessing information or reports related to a different medical device. For example, a reviewer can launch a first instance of the application to view reports related to patients that have been prescribed a therapeutic medical device and launch a second instance of the application to view reports related to patients that have been prescribed a monitoring medical device. The reviewer can launch the first and second instances of the applications during a single reviewing session, thereby providing the reviewer with the option of switching between the instances to view the two groups of patients, i.e., a first group including patients prescribed a therapeutic device and a second group including patients prescribed a monitoring medical device. In certain implementations, the end user terminal can be configured to open multiple instances upon opening the application such that the reviewer has access to all groups of patients. In some examples, the end user terminal can be configured to launch a single instance in response to a user selection of which group of patients to access. Upon selecting another group to review, the end user terminal can be configured to launch another instance of the application.

In certain implementations, the reviewer can review all the information transmitted by the medical device controller 120 or monitored during patient's use of the device. For example, the reviewer can use the reviewed data to generate reports that are then sent to the patient management system 630. For example, the reviewer interface may include one or more of patient and/or event information, display tools, editing tools, and ECG graphs and related tools.

The technician or reviewer can prepare a patient report based on the obtained physiological information. In preparing the report, the technician or reviewer can, for example, manipulate relevant portions of the physiological information to make relevant portions of physiological information easier for the end user to identify and review. The technician or reviewer can also edit portions of data, such as segments of an ECG signal, and provide annotations about which portions of the ECG show different types of events. The report can also include other patient information and/or statistics determined from the total monitoring period (e.g. percentage of time in a particular cardiac condition, total patient wear time, etc.). Other statistics or metrics that can be included in the patient report can include, for example, percentage of time in atrial fibrillation, percentage of time with bradycardia, percentage of time with tachycardia, average heart rate, most common symptom reported by the patient, number of identified events, and a number of treatments by a therapeutic medical device.

In some examples, the reviewer can also review patient/event information including patient data and/or event descriptions. For example, an event description can include a type of event (e.g., atrial fibrillation onset, atrial fibrillation offset, tachycardia onset, tachycardia offset, bradycardia onset, bradycardia offset, a pause in the monitoring, a manually patient-initiated event, and a doctor-requested event, such as when a caregiver requests the patient to perform an action, or where the event is remotely triggered on by or on behalf of the caregiver). In an implementation, an event that the medical device controller 120 detected can be automatically displayed to the reviewer as the default. If the reviewer, on reviewing the event, decides the detected event is incorrect or not an event, he or she can select the correct type event from, e.g., a drop-down list. When a new event is selected, in some examples, a confirmation pop-up screen can be displayed. After change is confirmed, the current event type can be crossed out and the new type displayed. In this manner, when a report is generated, the physician can see the original event, and the reviewer's changes and any explanations, if necessary. Once a report is completed, the data analysis site 610 and/or reviewer interface module 615 can transmit the report to the patient management server 625 and/or to the patient management system 630 for review by the end user.

In certain implementations, physiological information from the medical device controller 120 can also be transmitted directly or indirectly to the data processing module 620. In some examples, the data processing module 620 can be configured to automatically analyze the physiological information, such as portions of an ECG signal, using algorithms that provide an indication of patient status and/or cardiac function. For example, a non-limiting list of statistics that can be calculated based on a measured ECG signal include: premature ventricular contraction (PVC) count, heart rate information, heart sounds data, ECG data (e.g., continuous ECG data), lung fluid measurements/data, patient thoracic impedance measurements/data, pectoral impedance measurements/data, blood pressure, temperature, blood glucose levels, and blood oxygen levels. The calculated statistics can be included in a separate automatically generated patient report. Alternatively, statistics calculated by the data processing module 620 can be forwarded to the reviewer or reviewer interface module 615 and can be combined with the manually prepared patient report. The reviewer can also use the statistics during his or her review of the acquired physiological data.

In some examples, the data processing module 620 can be configured to apply predictive algorithms to the measured physiological information to provide an estimation or prediction for occurrence of a potential medical event for a subject within an associated period of time. The estimation or prediction can be provided in the form of a risk score which can be based on, for example, physiological measurements extracted from the ECG signal including heart rate variability, PVC burden or counts, activity, noise quantifications, atrial fibrillation, momentary pauses, heart rate turbulence, QRS height, QRS width, changes in the size or shape of the morphology, cosine R-T, artificial pacing, corrected QT interval, QT variability, T wave width, T wave alternans, T-wave variability, ST segment changes, early repolarization, late potentials, fractionated QRS, or fractionated T wave content. The risk score can indicate, for example, that a patient condition is generally improving, worsening, or remaining stable. Further, risk score values can be used to determine an appropriate course of treatment or, for example, to determine or suggest whether a patient should be admitted or, if already admitted, should remain in a hospital.

In certain implementations, once a report is prepared by the reviewer or automatically created at the data processing module 620, it can be sent to the patient management server 625 for processing and can be accessed by the end user through the patient management system 630. In some examples, data from the medical devices can be routed to the patient management server 625 with minimal or no processing at either the reviewer interface module 615 or the data processing module 620.

In certain implementations, the report can be stored in a remote data storage medium such as database 635, having one or more data structures corresponding to the values in the reports. As shown in FIG. 6, database 635 can be operable connected to patient management server 625. However, in certain implementations, the database 635 can be implemented as a component of the patient management server 625. Similarly, in some examples, the database 635 can be implemented as a database that is accessible to additional components such as the data processing module 620, the data analysis site 610, and the patient management system 630. In some implementations, the database 635 can include additional programming instructions or code for further processing information. For example, as described below in additional detail, the database 635 can include lookup tables for assigning a zone ranking to a patient, coded schemes or other instructions for determining and assigning a zone ranking to a patient, machine learning components such as training populations for training machine learning tools to be used in determining and assigning a zone ranking to a patient, and other similar computational tools and data sets for assisting in the determination and assigning of a zone ranking to a patient.

The information or document provided to the end user (e.g., a patient's physician) is referred to herein as a patient report. However, it is understood that, in some examples, data and/or physiological information can be sent directly from the medical device controller 120 to the patient management server 625 for further processing without being analyzed, edited, or modified at one of modules 615, 620. Thus, in some examples, raw or un-analyzed physiological data can be provided to the patient management system 630. In other examples, the measured physiological information can undergo limited filtering or processing to improve readability or clarity, but further analysis of the measured data can be performed at the patient management server 625 and/or the patient management system 630 either automatically or manually by the user. In other examples, the patient report can only include a particular subset of physiological information that would be of interest to the end user. In still other examples, the report can include only analysis, such as a percentage of time in atrial fibrillation, and no actual physiological data as collected by the medical device.

The patient reports can be provided to the patient management system 630 either periodically or at aperiodic intervals, such as in response to a particular event or action by the patient, treating physician, or another interested party. Additionally, a report can be generated in response to the patient's physiological data indicating that the patient has transitioned from one zone-based ranking to another as described above. For example, reports can be generated and provided to the patient management system 630 in response to a specific event (as opposed to being generated on a regularly-occurring basis or the end of device use), and delivered to the reviewing physician. In some examples, one or more triggering events can be as follows: Atrial Fibrillation, Tachycardia, Bradycardia, Pause, Patient-initiated, and Baseline.

In some examples, physicians are able to request reports corresponding to a specific time frame during device use or according to specific criteria being met (e.g., a transition from a first zone-based ranking to another zone-based ranking as described herein). The time frame of these reports may or may not correspond to a manual or automatically triggered event. In certain implementations, for each day of cardiac monitoring use, a summary report can be compiled and delivered to the physician including information on automatic and patient-triggered cardiac events as well as daily ECG metrics. In some examples, end of use reports can be compiled upon completion of a cardiac monitoring service, summarizing cardiac event findings and ECG trending metrics over the entire wear period. Such reports can summarize all findings during the report period (e.g., throughout wear time).

As discussed herein, in certain implementations the patient management system 630 can be configured to receive patient reports for different patients and to allow the end user to view the reports based on various selecting criteria or other factors. For example, the patient management system 630 can be configured to receive patient reports from different types of monitoring devices, from patients suffering from a variety of different physiological conditions, and/or for patients associated with different locations or hospitals. The patient management system 630 allows the end user to select which types of reports are viewed at a particular time.

When implemented into a zone-based ranking system as described herein, one or more of the remotely located modules as described herein in reference to FIG. 6 above can be used to monitor a patient's physiological information (e.g., as received from the medical device controller 120) to determine what zone-based ranking(s) a patient is currently in and if the patient transitions from a first zone-based ranking to another zone-based ranking according to the processes and techniques as described herein.

Figure 7:
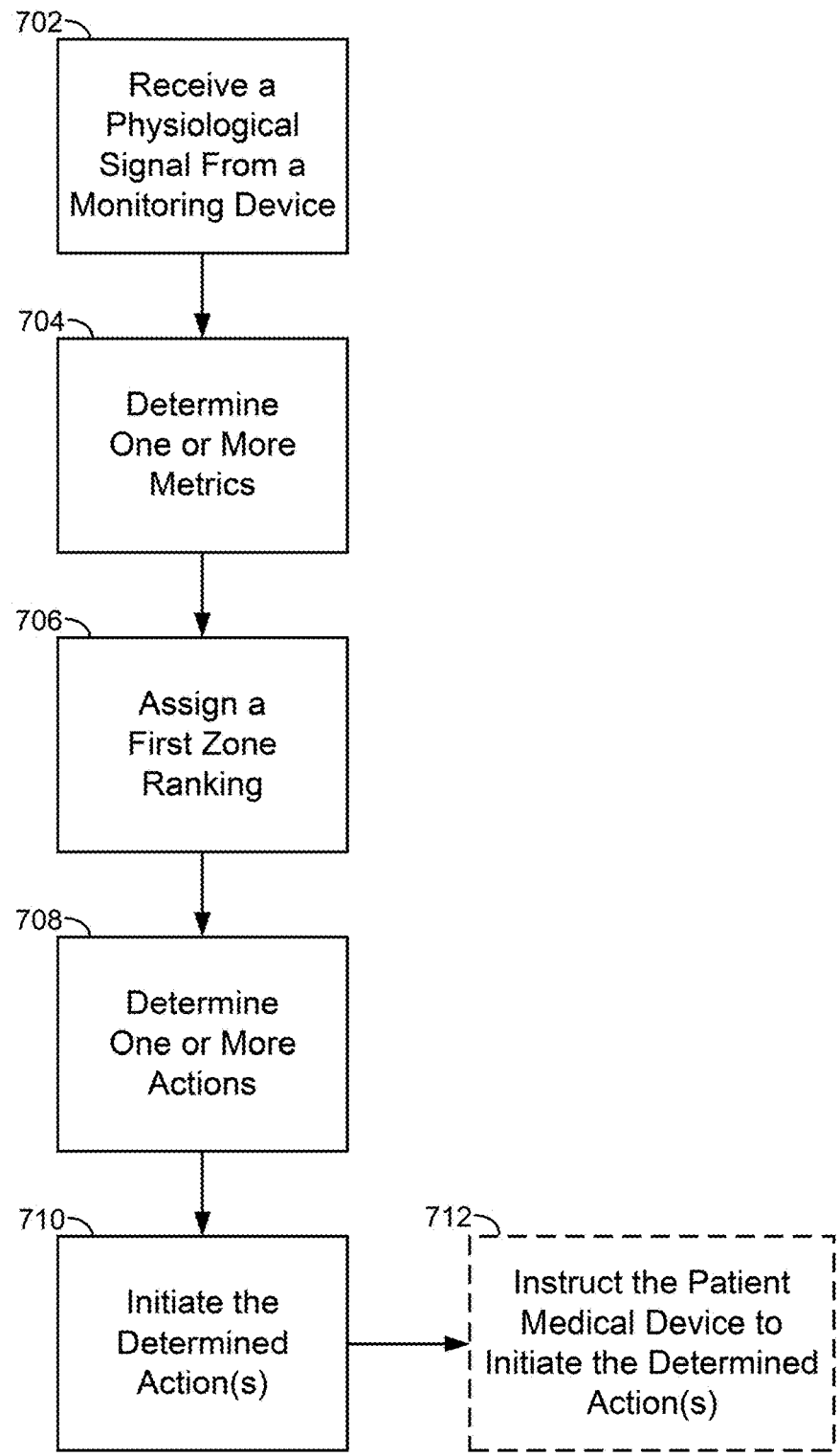
FIG. 7 illustrates a sample process for remotely determining a zone ranking and one or more actions for a patient, in accordance with an example of the present disclosure.

FIG. 7 illustrates a sample flowchart showing a process for determining a zone-based ranking and action for a patient wearing an ambulatory medical device, the determination and related processing being performed by a remote computing device (e.g., patient management server 625 as described above) that is operably connected to the medical device controller of the patient's ambulatory medical device.

The remote server can be configured to receive 702 recorded physiological data from a medical device controller (e.g., medical device controller 120 as described above). For example, the remote server can be configured to receive 702 raw digital data as recorded by the medical device controller. In some implementations, prior to transmitting the physiological data, the medical device controller can be configured to perform some preprocessing on the recorded physiological data. For example, the medical device controller can be configured to filter the recorded physiological data to focus the recorded data on one or more areas of interest. Similarly, the medical device controller can include processing circuitry to reduce or eliminate noise in the recorded physiological data.

Depending upon additional criteria such as, for example, available bandwidth, the medical device controller can be configured to adjust the resolution at which the recorded physiological data is transmitted. For example, if a high bandwidth connection is available, the medical device controller can be configured to transmit the recorded at full, or near-full, resolution. In certain implementations, the medical device controller can be configured to record the physiological data at 800 Hz. If a high bandwidth connection is available between the medical device controller and the remote server, the medical device controller can transmit the full resolution recorded data. In certain implementations, if there is a lower bandwidth connection available, the medical device controller can be configured to transmit the recorded physiological data at a lower resolution (e.g., 400 Hz). In certain implementations, the medical device controller can be configured to transmit the recorded physiological data at a lower resolution unless otherwise instructed to transmit at a higher resolution by the remote server.

The remote server can analyze the physiological signal to determine 704 one or more parameters or metrics indicated or quantified within the physiological signal. The one or more metrics can be indicative of the current cardiac state of the patient. In certain implementations, the one or more metrics can include the heartrate or change in heartrate of the patient, blood pressure of the patient, heartrate stability, changes in conduction vector of the heart, heart sounds information, and other similar metrics such as those listed above.

Based upon the one or more metrics, the remote server can assign 706 a first zone ranking for the patient. As noted above (e.g., in the description of FIG. 3), zone ranking can include a zone identifier (e.g., zone 1, zone 2, zone 3) as well as an associated severity level. For example, zone 1 can be associated with a low severity level, zone 2 can be associated with a medium severity level, and zone 3 and higher can be associated with a high severity level. Similarly, each severity level can have an associated set of one or more actions to initiate. Zone rankings, severity levels and associated actions are described in greater detail below in the specific examples.

Depending upon the implementation of the zone-based ranking system, a single zone ranking can be associated with the patient. For example, the current determined levels for the one or more metrics can be averaged together to assign a single zone ranking. In other implementations, the patient can be assigned a zone ranking for each metric measured, and the assigned zone ranking with the highest associated severity level can be prioritized such that any actions associated with that zone ranking are implemented first.

In order to assign a zone ranking to a patient, the remote server can use one or more data analysis and determination techniques. For example, the remote server can access a lookup table to determine an associated zone for a particular determined metric. The lookup table can be stored locally or at a centralized location such as database 635 discussed above in regard to FIG. 6. Using a lookup table to assign a zone is discussed in greater detail in the discussion of FIGS. 8-11 below.

Additional techniques can be used to assign a zone ranking to a patient. For example, a set of logic instructions such as a string of "if-then" statements can be used to step through each potential metric (as determined above) and value for those metrics. In certain implementations, the "if-then" statements can be organized as a set of nested loops and implemented as a programming library or other similar module.

Another technique can include using machine learning tools to model patterns based upon historical data and classify future conditions based upon the historic models. In some implementations, one or more machine learning tools such as a machine learning classifier can be trained on a large population, for example, a population that can range from several thousand to tens of thousands of patient records comprising electrophysiology, demographic and medical history information. The machine learning tools can include, but are not limited to, classification and regression tree decision models, such as random forest and gradient boosting, (e.g., implemented using R or any other statistical/mathematical programming language). In certain implementations, other classification based machine learning tools can be used, including neural networks and support vector machines. In some examples, after training, the machine learning classifier can be validated and a specificity value for the machine learning classifier can be determined. During validation, a separate validation population can be used to determine the accuracy, reliability, and associated specificity value for the machine learning classifier. In certain implementations, because the machine learning tools can be computationally intensive, some or all of the processing for the machine learning tools may be performed on a server that is separate from the medical device.

Referring again to FIG. 7, the remote server can determine 708 one or more actions based upon the assigned first zone ranking. For example, the one or more actions can include provide a treatment to the patient, activate an alarm indicating a potential treatment, provide instructions to the patient, record a portion of the patient's ECG signal, contact emergency services or the patient's physician, perform additional analysis of the patient's ECG signal, and other various actions. Once determined, the remote server can initiate 710 the one or more determined actions.

Depending upon the determined action, the remote server can instruct the patient's ambulatory medical device to perform the action. For example, if the determined action is to record a portion of the patient's ECG signal at a higher resolution, the remote server can instruct 712 the patient's ambulatory medical device to record at the higher resolution. Conversely, if the remote server is configured to perform the determined action, the remote server can initiate 710 the determined action without providing instruction to the patient's device. For example, if the determined action is to contact the patient's physician, the remote server can initiate 710 that action directly.

As noted above, an assigned zone ranking can also have an associated severity level. Additionally, when assigning a zone ranking to a patient, the remote server can also determine a confidence level according to a process similar to that shown in, for example, FIG. 4. As noted above, the confidence level can be used to determine whether an action is appropriate for a specific assigned zone ranking at a particular time. For example, when a zone ranking is assigned that has a high severity level with a treatment action associated (e.g., provide a defibrillation pulse), the remote server can perform an additional analysis to confirm that the assigned zone ranking is accurate and that the recommended action is appropriate.

The following examples illustrate sample scenarios where one or more portions of ECG signals and/or other physiological signals are used to determine a zone-based ranking and one or more actions to initiate for a specific patient. As described above, the processing and determination of the zone-based rankings and associated actions can be performed by a medical device controller integrated into or operably connected to a patient's ambulatory medical device (e.g., a monitoring unit for a mobile cardiac telemetry device). Additionally, in certain implementations, the processing and determination of the zone-based rankings and associated actions can be performed by a remote computing device such as a remote patient management server that is operably connected to the patient's ambulatory medical device. As such, it is to be understood that the following examples can be performed by either the medical device controller, a remote computing device, or a combination of the two where both the medical device controller and the remote computing device operate in concert to perform the processes illustrated in the following examples.

Example: Heartrate Monitoring

Figure 8:
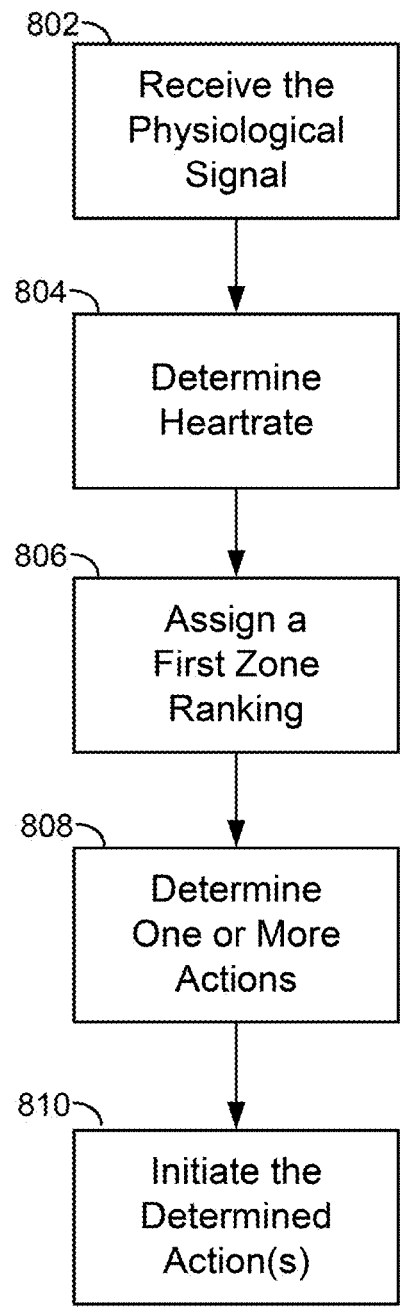
FIG. 8 illustrates a sample process for assigning a zone ranking to a patient when using heartrate as a determining metric, in accordance with an example of the present disclosure.

FIG. 8 illustrates a specific example of determining a zone ranking for a patient by monitoring the patient's heartrate. A processing device, e.g., wearable medical device controller 120 or a remote server such as patient management server 625, can receive 802 a physiological signal from one or more components of the medical device such as one or more sensing electrodes and/or conditioning circuitry configured to condition a signal measured by the one or more sensing electrodes. The processing device can analyze the physiological signal to determine 804 a heartrate for the patient. Based upon the heartrate, the processing device can assign 806 a first zone ranking for the patient.

In order to assign 806 a zone ranking for the patient, the processing device can access, for example, a local lookup table including information related to heartrate values and associated zone rankings for specific heartrate values. The local lookup table can be stored in a computer readable storage medium in communication with the processing device, for example, one or more databases.

Once the zone ranking is assigned, the processing device can determine 808 one or more actions associated with that zone ranking. As noted above, each zone ranking has an associated severity level and one or more actions to initiate. To determine 808 the one or more actions, the processing device can access the local lookup table which can include an entry for one or more actions associated with each individual zone ranking. As such, the local lookup table for heartrate can resemble table 500 as shown in FIG. 5, with additional information such as heartrate ranges associated with each zone ranking. An example of a heartrate lookup table is shown in table 900 as illustrated in FIG. 9.

As shown in table 900, various zone rankings can be provided for assigning a zone ranking based upon heartrate monitoring. Zone 1 can be associated with a heartrate between 31 and 89 beats. Depending upon the patient, this range can be considered normal and, as such, can have no associated severity level. Similarly, there may be no associated immediate or long-term actions beyond continued monitoring of the patient. The table 900 can include a set of rapid heartrate zones Zone 2-Zone 5. The rapid heartrate zones can be defined as being a rate higher than the upper limit of the normal zone, e.g., Zone 1. The table 900 can also include a set of slow heartrate zones Zone 6 and Zone 7. The slow heartrate zone rankings can be defined as being a rate slower than the lower limit of the normal zone.

As shown in table 900, Zone 2 can be associated with a heartrate of between 90 and 119 beats per minute and can have a low associated severity risk. As a result of the low risk, the associated immediate action can be continued monitoring of the patient and the long-term response can be to capture additional ECG signal recordings for later review. Zone 3 can be associated with a heartrate of between 120-169 beats per minute and can have a medium associated severity risk. As a result of the medium risk, the associated immediate action can be to provide instructions to the patient regarding their accelerated heartrate (e.g., stop doing any strenuous activity) and the long-term response can be to capture additional ECG signal recordings and perform additional ECG analysis. Zone 4 can be associated with a heartrate of between 170 and 200 beats per minute and can have a high associated severity risk. As a result of the high risk, the associated immediate action can be to prepare the device for treatment (e.g., charge one or more capacitors for delivering a therapeutic shock) and the long-term response can be to notify the patient's physician that they are experiencing tachycardia. Zone 5 can be associated with a heartrate of over 200 beats per minute and can have a very high associated severity risk. As a result of the very high risk, the associated immediate action can be to provide treatment to the patient (e.g., anti-tachycardia pacing or a defibrillation shock) and the long-term response can be to notify emergency personnel.

For the slow heartrate zone rankings, Zone 6 can be associated with a heartrate of between 20 and 30 beats per minute and can have a high associated severity risk as the patient is likely to lose consciousness as a result of bradycardia onset. As a result of the high risk, the associated immediate action can be to prepare the device for treatment (e.g., charge one or more capacitors for delivering a therapeutic shock) and the long-term response can be to notify the patient's physician that they are likely experiencing bradycardia. Zone 7 can be associated with a heartrate of under 20 beats per minute and can have a very high associated severity risk. As a result of the very high risk, the associated immediate action can be to provide treatment to the patient (e.g., provide bradycardia pacing) and the long-term response can be to notify emergency personnel.

It should be noted that the heartrate rages, zone rankings and associated severity levels and actions are provided by way of example only. Depending upon an individual patient and their ongoing treatment, various changes can be made to the data represented in table 900.

Additionally, other factors such as physical activity can be used to determine what heartrate ranges are associated with what zone rankings. For example, a wearable medical device can include one or more accelerometers that are configured to measure whether the patient wearing the medical device is currently exercising or doing some other physical activity. If physical activity is detected, the heartrate ranges can be adjusted accordingly to compensate for increased cardiac activity as a result of the activity. For example, an alternate heartrate lookup table can be provided in the medical device for physical activity. In the alternate table, Zone 1 (the normal zone ranking) may have an adjusted heartrate of 31-119 to account for the physical activity. The additional high heartrate zone rankings can then be adjusted accordingly.

Referring again to FIG. 8, the processing device can initiate 810 the determined one or more actions for the assigned zone ranking and, based upon the one or more actions, continue monitoring the patient.

Additional parameters that can be determined from a patient's heartrate can also be used to determine what zone ranking a patient should be assigned. For example, onset time for tachycardia or bradycardia can be used to determine a zone ranking and severity level.

Example: Stability Monitoring

Figure 10:
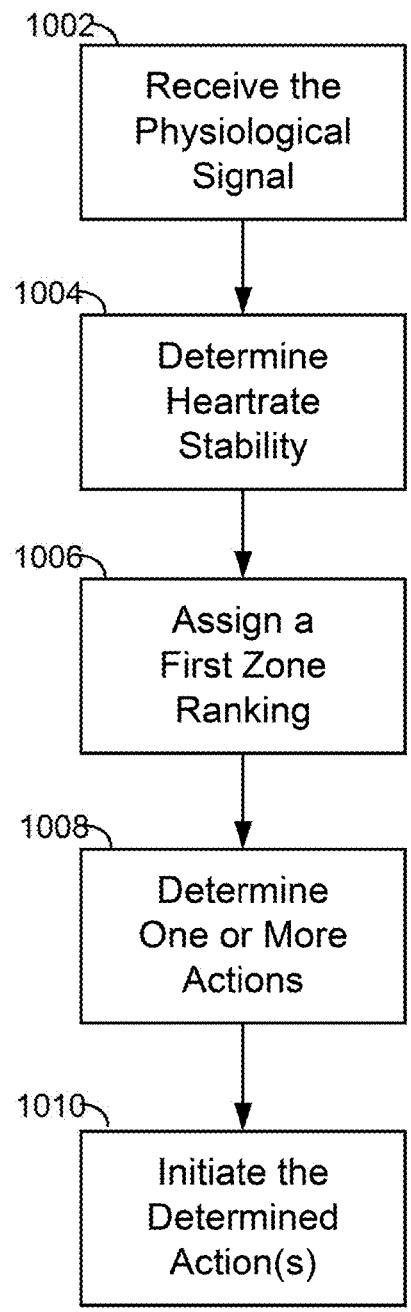
FIG. 10 illustrates a sample process for assigning a zone ranking to a patient when using heartrate stability as a determining metric, in accordance with an example of the present disclosure.

FIG. 10 illustrates a specific example of determining a zone ranking for a patient by monitoring the patient's heartrate stability. Stability is a measurement of the regularity of a patient's heartbeat. During a normal VT, a patient's heartrate is monomorphic and the associated heartrate stability is stable. When analyzing a patient's heartrate stability, stability can be measured as a percent change in the heartrate intervals over time. Typically, a high heartrate stability indicates a stable or slightly changing heartrate interval (e.g., plus or minus 5% over a particular period of time such as 1 minute). Conversely, a low heartrate stability can indicate a cardiac event as, during certain cardiac events, a patient's heartrate stability level can vary greatly. For example, Torsades is a VT evidenced in patients with a long QT interval. It is characterized by rapid, irregular QRS complexes, which appear to be twisting around the ECG baseline. This arrhythmia can cease spontaneously or degenerate into ventricular fibrillation. However, based upon the irregular QRS complexes, a cardiac event such as Torsades has a low heartrate stability rating as the timing between heartbeats is changing constantly. As such, a cardiac event such as Torsades can be identified, or likely identified, based upon analyzing a patient's stability rating. Additionally, for example, analyzing a patient's heartrate stability can be used to identify atrial fibrillation.

Referring to FIG. 10, the processing device can receive 1002 a physiological signal from one or more components of the medical device such as one or more sensing electrodes and/or conditioning circuitry configured to condition a signal measured by the one or more sensing electrodes. The processing device can analyze the physiological signal to determine 1004 a heartrate stability measurement for the patient. Based upon the stability measurement, the processing device can assign 1006 a first zone ranking for the patient.

In order to assign 1006 a zone ranking for the patient, the processing device can access, for example, a local lookup table including information related to heartrate stability values and associated zone rankings for specific heartrate stability values. The local lookup table can be stored in a computer readable storage medium in communication with the processing device in, for example, a data structure such as a database. In certain implementations, the local lookup table can be dynamically populated with zone parameters used to define the zone rankings. For example, a physician or other caregiver can assign specific parameters for each zone ranking based upon heartrate stability baseline information for a patient as well as the patient's cardiac history.

Once the zone ranking is assigned, the processing device can determine 1008 one or more actions associated with that zone ranking. As noted above, each zone ranking has an associated severity level and one or more actions to initiate. To determine 1008 the one or more actions, the processing device can access the local lookup table which can include an entry for one or more actions associated with each individual zone ranking. For example, based upon the severity of the stability measurement, the processing device may determine that the patient should be administered anti-tachycardia pacing pulses. The processing device can initiate 1010 the determined one or more actions for the assigned zone ranking and, based upon the one or more actions, continue monitoring the patient.

Example: Conduction Vector Monitoring

Figure 11:
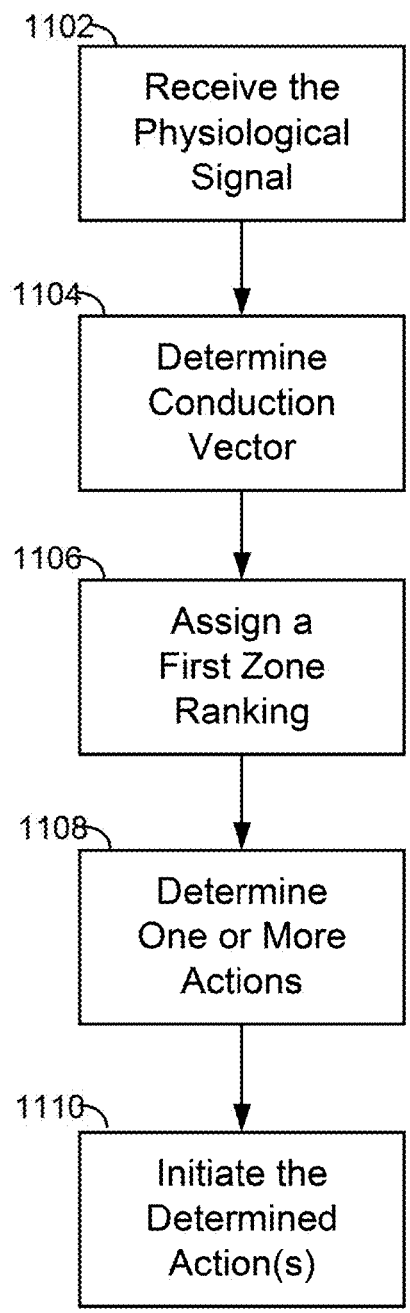
FIG. 11 illustrates a sample process for assigning a zone ranking to a patient when using a conduction vector as a determining metric, in accordance with an example of the present disclosure.
Figure 12A:
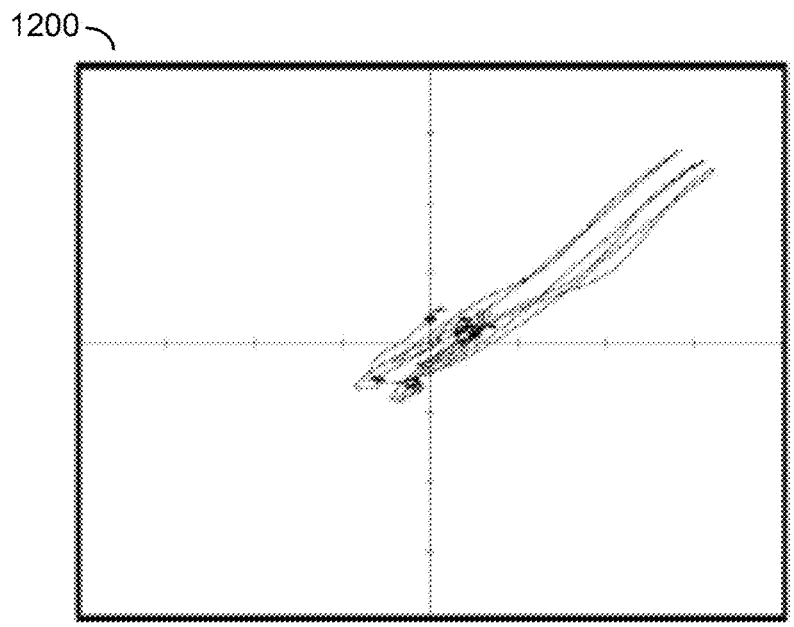
FIGS. 12A and 12B illustrate sample conduction vectors as measured for a patient, in accordance with an example of the present disclosure.
Figure 12B:
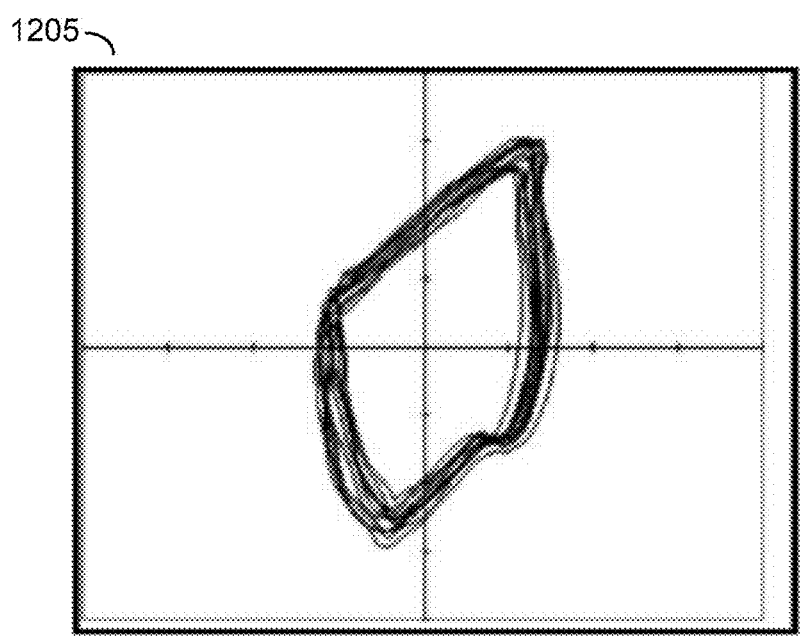

FIG. 11 illustrates a specific example of determining a zone ranking for a patient by monitoring the patient's conduction vector. Typically, a patient's conduction vector is represented by a vector showing the electrical pulses moving diagonally back and forth, which an abnormal conduction vector shows the electrical pulses moving side-to-side or in a rotational direction. For example, FIGS. 12A and 12B illustrate sample conduction vector plots for a patient. FIG. 12A illustrates a stable conduction vector plot 1200 for a patient. Such a plot can be expected when a patient is experience normal cardiac function. A stable conduction vector such as plot 1200 shown in FIG. 12A can be stored as a baseline conduction vector plot for a patient, the baseline plot being used as a starting point when comparing future conduction vector plots (e.g., plots obtained at a time after the baseline plot was obtained) to determine any changes in the patient's measured conduction vector. For example, FIG. 12B illustrates a sample conduction vector plot showing a patient experiencing VT. As shown in plot 1205, the conduction vector is plotted in a rotational direction on the plot, indicating abnormal cardiac function.

One type of abnormal condition indicated by monitoring a patient's conduction vector is re-entry tachycardia, where the atrial nodes continue to function properly but are unable to adequately move blood as a result of the abnormal conduction of the hear. Such a condition can lead to VT transitioning to VF, sustained VT for an extended period of time, or the heart directly going into VF.

Referring again to FIG. 11, the processing device can receive 1102 a physiological signal from one or more components of the medical device such as one or more sensing electrodes and/or conditioning circuitry configured to condition a signal measured by the one or more sensing electrodes. The processing device can analyze the physiological signal to determine 1104 a conduction vector for the patient, the conduction vector indicative of stable conduction at the heart or abnormal conduction. Based upon the conduction vector, the processing device can assign 1106 a first zone ranking for the patient.

In order to assign 1106 a zone ranking for the patient, the processing device can access, for example, a local lookup table including information related to conduction vector readings and associated zone rankings for specific conduction vectors. The local lookup table can be stored in a computer readable storage medium in communication with the processing device in, for example, one or more databases. In certain implementations, the local lookup table can be dynamically populated with zone parameters used to define the zone rankings. For example, a physician or other caregiver can assign specific parameters for each zone ranking based upon conduction vector baseline information for a patient as well as the patient's cardiac history.

Once the zone ranking is assigned, the processing device can determine 1108 one or more actions associated with that zone ranking. As noted above, each zone ranking has an associated severity level and one or more actions to initiate. To determine 1108 the one or more actions, the processing device can access the local lookup table which can include an entry for one or more actions associated with each individual zone ranking. For example, based upon the severity of the conduction vector, the processing device may determine that the patient should be administered anti-tachycardia pacing pulses of a defibrillation pulse. The processing device can initiate 1110 the determined one or more actions for the assigned zone ranking and, based upon the one or more actions, can continue to monitor the patient.

Example: Heart Sounds Monitoring

Figure 13:
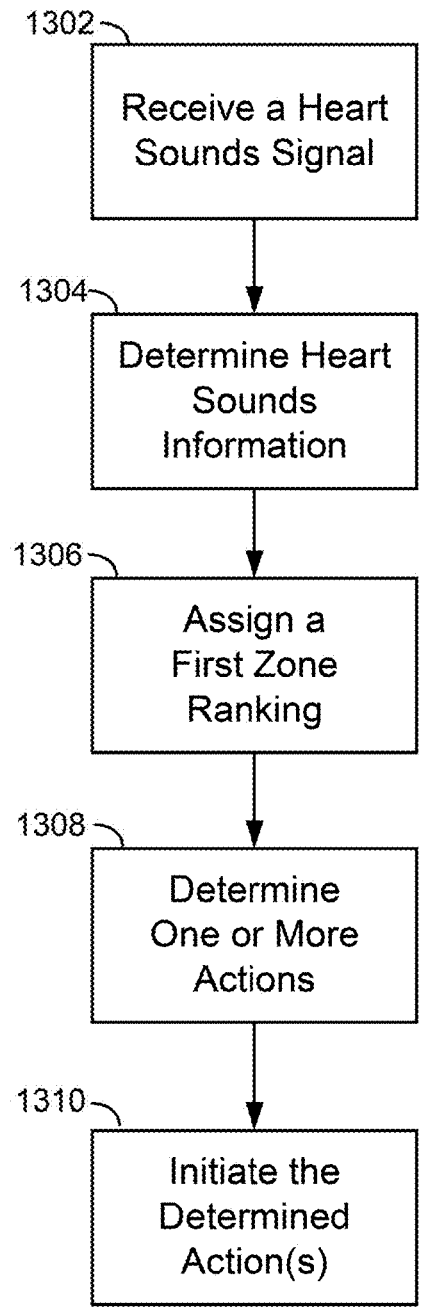
FIG. 13 illustrates a sample process for assigning a zone ranking to a patient when using heart sounds information as a determining metric, in accordance with an example of the present disclosure.

FIG. 13 illustrates a specific example of determining a zone ranking for a patient by monitoring the patient's heart sounds information. The heart sounds information can be collected by, for example, an acoustic sensor positioned adjacent to or integrated into one or more electrodes of the wearable medical device. The processing device can receive 1302 a heart sounds signal from one or more acoustic sensors of the medical device. The processing device can analyze the heart sounds signal to determine 1304 a heart sounds information for the patient, the heart sounds information including S3 and S4 heart sounds information as well as EMAT information.

In order to assign 1306 a zone ranking for the patient, the processing device can access, for example, a local lookup table including information related to heart sounds information (e.g., average EMAT values over a specific period of time) and associated zone rankings for specific heart sounds information. For example, a zone ranking can be associated with an EMAT average value of above 14 and below 16 for a time period (e.g. 3 days), a zone ranking for an EMAT value above 16, and a zone ranking for an EMAT value below 14. The local lookup table can be stored in a computer readable storage medium in communication with the processing device in, for example, one or more databases.

Once the zone ranking is assigned, the processing device can determine 1308 one or more actions associated with that zone ranking. As noted above, each zone ranking has an associated severity level and one or more actions to initiate. To determine 1308 the one or more actions, the processing device can access the local lookup table which can include an entry for one or more actions associated with each individual zone ranking. For example, based upon presence of S3 and S4 heart sounds, or a value of the patient's average EMAT over a period of time, the processing device may determine 1308 that one or more actions are appropriate. To continue the above example, the zone ranking having an average EMAT value over 16 can include admit the patient to the hospital as an associated action, the zone ranking having an average EMAT value between 14 and 16 can include change the patient's medication as an associated action, and the zone ranking having an average EMAT value under 14 can include continue monitoring the patient as an associated action.

The processing device can initiate 1310 the determined one or more actions for the assigned zone ranking and, based upon the one or more actions, can continue to monitor the patient.

As noted above, a combination of ranking techniques can be used to assign a zone ranking to a patient. For example, each of heartrate, stability, conduction vector and heart sounds monitoring can be used to assign a patient a zone ranking. For example, each individual metric can be analyzed individually and a zone ranking assigned to the patient for each of the metrics. The processing device can then analyze the assigned zone rankings to determine which assigned zone ranking has the highest severity level and can initiate the one or more actions associated with that zone ranking. Thus, for example, if a patient has a heartrate zone ranking that is very high severity, a stability zone ranking that is medium severity, a conduction vector zone ranking that is high severity, and a heart sounds zone ranking that is medium severity, the heartrate zone ranking can take precedence and the patient can be treated with one or more actions associated with a very high severity level.

Alternatively, the individual metrics can be weighted and an algorithm can be used to combine the individual zone rankings into an overall zone ranking. For example, the individual metric zone rankings can be weighted and added together such that they produce a result between 0.0 and 1.0. The higher the overall zone ranking (e.g., the closer to 1.0 the overall zone ranking value is), the higher the severity level.

In some examples, additional criteria, metrics or parameters can be used to determine a patient's zone ranking. In certain implementations, a patient's progression through a specific disease classification can be used to weigh one or more of the metrics or parameters as listed above, or as a separate metric or parameter altogether. For example, a patient's zone ranking can be impacted by the patient's classification in the New York Heart Association (NYHA) Functional Classification for heart disease. Similarly, additional metrics such as frequency of detection (e.g., how often is a patient assigned a specific zone ranking) and duration of events (e.g., how long is a patient assigned a specific zone ranking) can be used in weighing individual metrics or parameters to determine an overall zone ranking for the patient.

Additionally, in certain implementations, individual metrics can be used as fallback metrics in the event that a particular reading is unreliable. For example, if an ECG signal appears to have a high level of noise and is likely to produce unreliable information, one or more additional metrics such as conduction vector, heart sounds and stability can be used to determine current cardiac function for the patient.

Although the subject matter has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment may be combined with one or more features of any other embodiment

What is claimed is:

1. A system for assigning zone rankings to a patient, the system comprising:
    a remote computing device in communication with an external wearable medical monitoring device, comprising
        at least one database, and
        a processor in communication with the at least one database configured to
        receive at least one ECG signal from the external wearable medical monitoring device worn by the patient,
        assign a normal zone ranking to the patient based upon baseline patient data stored on the at least one database,
        determine one or more metrics from the at least one ECG signal of the patient, wherein determining one or more metrics comprises determining a heart rate of the patient,
        assign a first zone ranking to the patient based upon the heart rate, the first zone ranking selected from a plurality of zone rankings stored on the at least one database,
        determine one or more actions to initiate at the external wearable medical monitoring device based upon the assigned first zone ranking, and
        initiate the one or more determined actions at the external wearable medical monitoring device, the one or more determined actions comprising at least one of
        changing one or more monitoring thresholds for monitoring the patient for an arrhythmia condition based on a change in heart rate relative to baseline patient data of the normal zone ranking,
        changing one or more alarm profiles based on a change in heart rate relative to baseline patient data of the normal zone ranking, and
        changing one or more treatment thresholds for providing therapy to the patient relative to normal zone ranking treatment thresholds.

2. The system of claim 1, wherein the one or more determined actions further comprise at least one of providing a treatment to the patient at the external wearable medical monitoring device based on the changed one or more treatment thresholds, activating an alarm indicating a potential treatment based on the changed one or more changed alarm profiles, providing instructions to the patient, and performing additional analysis of the at least one ECG signal of the patient.

3. The system of claim 1, wherein the plurality of zone rankings comprises at least a set of rapid heart rate action zones and a set of slow heart rate action zones.

4. The system of claim 3, wherein the set of rapid heart rate action zones comprises at least a first rapid heart rate zone comprising a heart rate of 90-119 beats per minute, a second rapid heart rate zone comprising a heart rate of 120-169 beats per minute, a third rapid heart rate zone comprising a heart rate of 170-200 beats per minute, and a fourth rapid heart rate zone comprising a heart rate over 200 beats per minute.

5. The system of claim 3, wherein the set of slow heart rate action zones comprises at least a first slow heart rate zone comprising a heart rate of 20-30 beats per minute and a second slow heart rate zone comprising a heart rate under 20 beats per minute.

6. The system of claim 1, wherein each of the plurality of zone rankings comprises a severity level.

7. The system of claim 6, wherein the severity level for each of the plurality of zone rankings comprises at least one of low risk, medium risk, high risk, and requires immediate attention.

8. An external wearable medical device comprising:
at least one database;
at least one ECG sensing electrode configured to detect at least one ECG signal of a patient; and
a monitoring device operatively connected to the at least one ECG sensing electrode, the monitoring device comprising a processor in communication with the at least one database and configured to
assign a normal zone ranking to the patient based upon baseline patient metrics stored in the at least one database,
receive the at least one ECG signal of the patient from the at least one ECG sensing electrode,
determine one or more metrics from the at least one ECG signal of the patient, wherein determining one or more metrics comprises determining a heart rate of the patient,
assign a first zone ranking to the patient based upon the heart rate, the first zone ranking selected from a plurality of zone rankings stored on the at least one database,
determine one or more actions to initiate based upon the assigned first zone ranking, and
initiate the one or more determined actions,
wherein the one or more determined actions comprise at least one of
changing one or more monitoring thresholds for monitoring the patient for an arrhythmia condition based on a change in heart rate relative to baseline patient data the normal zone ranking,
changing one or more alarm profiles based on a change in heart rate relative to baseline patient metrics of the normal zone ranking, and
changing one or more treatment thresholds for providing therapy to the patient relative to normal zone ranking treatment thresholds.

9. The external wearable medical device of claim 8, wherein the one or more determined actions further comprise at least one of providing a treatment to the patient based on the changed one or more treatment thresholds, activating an alarm indicating a potential treatment based on the changed one or more changed alarm profiles, providing instructions to the patient, and performing additional analysis of the at least one ECG signal of the patient.

10. The external wearable medical device of claim 8, wherein the monitoring device is further configured to analyze the heart rate to determine if the patient is experiencing one of bradycardia, ventricular tachycardia and ventricular fibrillation.

11. The external wearable medical device of claim 10, further comprising at least one therapy electrode operably connected to the monitoring device and configured to direct a therapeutic shock to the patient.

12. The external wearable medical device of claim 11, wherein the at least one therapy electrode is further configured to direct a defibrillation shock to the patient if the patient is experiencing ventricular fibrillation.

13. The external wearable medical device of claim 11, wherein the at least one therapy electrode is further configured to provide a pacing shock to the patient if the patient is experiencing bradycardia.

14. The external wearable medical device of claim 8, wherein each of the plurality of zone rankings comprises a severity level.

15. The external wearable medical device of claim 14, wherein the severity level for each of the plurality of zone rankings comprises at least one of low risk, medium risk, high risk, and requires immediate attention.

16. The external wearable medical device of claim 15, wherein initiating one or more determined actions comprises at least one of
recording the at least one ECG signal of that patient for a zone with a low risk,
recording the at least one ECG signal of the patient and additional patient information for a zone with a medium risk,
providing a pacing shock to the patient for a zone with a high risk, and
providing a defibrillation shock to the patient for a zone that requires immediate attention.

17. The external wearable medical device of claim 16, wherein providing a pacing shock comprises at least one of providing an antibradycardia pacing shock and providing an antitachycardia pacing shock.

18. The external wearable medical device of claim 8, further comprising a user display interface operably connected to the monitoring device and configured to provide information related to the one or more determined actions to the patient.

19. The external wearable medical device of claim 18, wherein the user display interface is configured to provide instructions to the patient.

20. The external wearable medical device of claim 8, further comprising an accelerometer to measure motion associated with the at least one ECG sensing electrode, wherein the monitoring device is configured to receive data representing the measured motion.

21. The external wearable medical device of claim 20, wherein the monitoring device is further configured to determine a level of exertion associated with the patient based upon the received data representing the measured motion and adjust a severity level associated with each of the plurality of zone rankings based upon the determined level of exertion.

22. A system for assigning zone rankings to a patient, the system comprising:
an external wearable medical device comprising
at least one ECG sensing electrode configured to detect at least one ECG signal of the patient, and
a monitoring device operatively connected to the at least one ECG sensing electrode and configured to
receive the at least one ECG signal of the patient from the at least one ECG sensing electrode, and
transmit the at least one ECG signal; and
a remote computing device comprising
a processor,
at least one database, and
a computer readable medium in communication with the at least one database and comprising one or more instructions that, when executed, cause the processor to
establish communications with the monitoring device, receive the at least one ECG signal from the monitoring device, assign a normal zone ranking to the patient based upon historical patient data stored on the at least one database, determine one or more metrics from the at least one ECG signal of the patient, wherein determining one or more metrics comprises determining a heart rate of the patient, assign a first zone ranking to the patient based upon the heart rate, the first zone ranking selected from a plurality of zone rankings stored on the at least one database, determine one or more actions to initiate based upon the assigned first zone ranking, and initiate the one or more determined actions, wherein the one or more determined actions comprise at least one of changing one or more monitoring thresholds for monitoring the patient for an arrhythmia condition based on a change in one or more heart rate relative to historical patient data of the normal zone ranking, changing one or more alarm profiles based on a change in one or more heart rate relative to historical patient data of the normal zone ranking, and changing one or more treatment thresholds for providing therapy to the patient relative to normal zone ranking treatment thresholds.

23. The system of claim 22, wherein initiating the one or more determined actions comprises instructing the external wearable medical device to perform the one or more determined actions.

24. The system of claim 22, wherein the one or more determined actions further comprise at least one of providing a treatment to the patient at the external wearable medical device based on the changed one or more treatment thresholds, activating an alarm indicating a potential treatment based on the changed one or more changed alarm profiles, providing instructions to the patient, and performing additional analysis of the at least one ECG signal of the patient.

25. The system of claim 6, wherein the processor is further configured to determine whether the severity level satisfies a severity threshold for a time period associated with the one or more determined actions, and wherein the processor performs the additional analysis and assigns a new zone ranking if the severity level does not satisfy the severity threshold for the time period associated with the one or more determined actions.

26. The system of claim 1, wherein
the processor is further configured to
determine a confidence level associated with the assignment of the first zone ranking,
determine whether the confidence level satisfies a confidence threshold for a time period associated with the one or more determined actions before initiating the one or more determined actions, and
perform the additional analysis and assign a new zone ranking if the confidence level does not satisfy the confidence threshold for the time period associated with the one or more determined actions.

27. The system of claim 1, wherein the one or more determined actions further include instructing the external wearable medical monitoring device to perform additional signal analysis or recording of signals detected by one or more sensors and associated circuitry for monitoring at least one of heart sounds data, lung fluid measurements/data, patient thoracic impedance measurements/data, pectoral impedance measurements/data, blood pressure, temperature, patient movement, blood glucose levels, and blood oxygen levels.

* * * * *

UNITED STATES PATENT AND TRADEMARK OFFICE
CERTIFICATE OF CORRECTION

PATENT NO.         : 10,470,702 B2
APPLICATION NO.    : 15/437954
DATED              : November 12, 2019
INVENTOR(S)        : Jason T. Whiting and Steven J. Szymkiewicz It is certified that error appears in the above-identified patent and that said Letters Patent is hereby corrected as shown below:

In the Specification

Column 14, Line 22, delete "of" - insert -- µf --
Column 19, Line 67, delete "patients" - insert -- patient's --
Column 22, Line 10, delete "625" - insert -- 625. --
Column 34, Line 5, after "embodiment" - insert -- . --

In the Claims

Claim 22 Column 37, Line 21, after "in" - delete "one or more"
Claim 22 Column 37, Line 25, after "in" - delete "one or more"

Signed and Sealed this
Eighteenth Day of February, 2020

Andrei Iancu
*Director of the United States Patent and Trademark Office*